United States Patent [19]

Akimoto et al.

[11] Patent Number: 5,496,822
[45] Date of Patent: Mar. 5, 1996

[54] COMPOUNDS AND METHODS FOR TREATING TUMORS

[75] Inventors: Hiroshi Akimoto, Kobe; Takenori Hitaka, Takarazuka, both of Japan

[73] Assignee: Takeda Chemical Industries, Ltd., Osaka, Japan

[21] Appl. No.: 308,500

[22] Filed: Sep. 21, 1994

Related U.S. Application Data

[63] Continuation of Ser. No. 219,735, Mar. 29, 1994, abandoned, which is a continuation of Ser. No. 990,370, Dec. 15, 1992, abandoned, which is a continuation of Ser. No. 630,984, Dec. 20, 1990, abandoned.

[30] Foreign Application Priority Data

Dec. 20, 1989 [JP] Japan .................................. 1-332110

[51] Int. Cl.$^6$ ....................... A61K 31/505; C07D 487/04
[52] U.S. Cl. ............................................. 514/258; 544/280
[58] Field of Search ........................... 544/280; 514/258; 546/113

[56] References Cited

U.S. PATENT DOCUMENTS

| | | | |
|---|---|---|---|
| 3,024,243 | 3/1962 | Song et al. | 546/113 |
| 3,320,268 | 5/1967 | Shen | 546/113 |
| 4,939,159 | 7/1990 | Anderson et al. | 546/113 |
| 4,996,206 | 2/1991 | Taylor et al. | 544/288 |
| 4,997,838 | 3/1991 | Akimoto et al. | 544/280 |
| 5,028,608 | 7/1991 | Taylor et al. | 514/288 |

FOREIGN PATENT DOCUMENTS

| | | |
|---|---|---|
| 0334636 | 9/1989 | European Pat. Off. |
| 0343801 | 11/1989 | European Pat. Off. |

OTHER PUBLICATIONS

CA 112:158968n by Akimoto et al (1990).
Journal of Medicinal Chemistry, vol. 28, 1985, pp. 914–921.

*Primary Examiner*—Mukund J. Shah
*Assistant Examiner*—Pavanaram K. Sripada
*Attorney, Agent, or Firm*—Foley & Lardner

[57] ABSTRACT

The compounds of the formula, $$\begin{array}{c}\text{X}\\\text{Q}^1 \diagup \diagdown\\\text{W} \diagdown \text{Q}^2 \diagup \text{N} \diagdown \text{Y}\\\text{H}\end{array}\text{—Z—}\text{\textcircled{B}}\text{—CONHCHCOOR}^1\\\phantom{xxxxxxxxxxxxxxxxxxxxxxxxxxx}\text{CH}_2\text{CH}_2\text{COOR}^2$$

wherein the ring A is a pyrrole ring which may be hydrogenated; —B— is a divalent cyclic or chain group which may be substituted; one of $Q^1$ and $Q^2$ is N, with the other being N or CH; W is a halogen or hydrogen atom or a group bonded to the bonding line with a carbon, nitrogen, oxygen or sulfur atom, provided that W is not —$NH_2$; X is an amino, hydroxyl or mercapto group; Y is a hydrogen atom or a hydroxyl or amino group; Z is a straight-chain divalent group having a number of atoms of 2 to 5 composed of carbon atoms which each may be substituted, or carbon atoms which each may be substituted and one hetero atom which may be substituted; —$COOR^1$ and —$COOR^2$ each is the same as or different from the other and represents a carboxyl group which may be esterified, or salts thereof are provided.

The compounds are produced by reacting compounds of the formula, $$\begin{array}{c}\text{X}\\\text{Q}^1 \diagup \diagdown\\\text{W} \diagdown \text{Q}^2 \diagup \text{N} \diagdown \text{Y}\\\text{H}\end{array}\text{—Z—}\text{\textcircled{B}}\text{—COOR}^3$$

wherein A, —B—, W, W, X, Y, $Q^1$ and $Q^2$ are the same as defined above, with compounds of the formula, $$\text{H}_2\text{N—CH—COOR}^1\\\phantom{xxxxxx}|\\\phantom{xxxxxx}\text{CH}_2\text{CH}_2\text{—COOR}^2$$

wherein —$COOR^1$ and —$COOR^2$ are the same as defined above, and useful as anti-tumor agents.

15 Claims, No Drawings

COMPOUNDS AND METHODS FOR TREATING TUMORS

This application is a continuation of United States application Ser. No. 08/219,735 filed Mar. 29, 1994 now abandoned; which is a continuation of Ser. No. 07/990,370 filed Dec. 15, 1992 now abandoned; which is a continuation of Ser. No. 07/630,984 filed Dec. 20, 1990 now abandoned.

This invention relates to novel condensed hetero-cyclic compounds which are useful as an anti-tumor agent and to a production process thereof.

Folic acid and its related compounds, as a transport agent in living body of C1 units derived from formic acid or formaldehyde, play a role as a coenzyme in a great variety of enzyme reactions, such as the nucleic acid biosynthesis, amino acid peptide metabolism and methane production systems. In the nucleic acid biosynthesis system, particularly, such compounds are essential for the C1 unit metabolism transfer reactions in the purine synthesis and thymidine synthesis pathways. In order for folic acid to demonstrate its biological activities, normally, it is required to undergo two steps of reduction to be transformed to its active coenzyme form. As a drug substance which binds strongly to the enzyme (dihydrofolate reductase) governing the second reduction step to thereby inhibit the reduction of dihydrofolate to tetrahydrofolate, there are known asomepterine (methotrexate: MTX) and its analogous compounds. These drug substances, that act to exert damage to DNA synthesis, eventually bringing about cell death, have been developed as an anti-tumor agent and occupy a clinically important position. Furthermore, reports have been made of the folic acid antagonists that work through a mechanism being different from the inhibition of dihydrofolate reductase, namely a tetrahydroaminopterine based anti-tumor agent (5,10-dideaza-5,6,7,8-tetrahydro-aminopterine: DDATHF) [Journal of Medicinal Chemistry, 28, 914 (1985)] which can act mainly through a mechanism to inhibit glycinamide ribonucleotide transformylase being involved in the initial stage of purine biosynthetic pathway or a quinazoline-based anti-tumor agent (2-desamino-2-methyl-10-propargyl-5,8-dideazafolate: DMPDDF) [British Journal of Cancer, 58, 241 (1988)] which can work principally through a mechanism to inhibit thymidylate synthetase participating in the conversion of 2-deoxyuridylic acid to thymidylic acid, and others. Besides those folic acid antagonists having a basic skeleton of a condensed ring of six-membered rings, on the other hand, it was also reported that the compounds composed of the pyrrolo[2,3-d]pyrimidine skeleton, or a condensed ring from a six-membered ring and a five-membered ring, exhibit antitumor activity, as well. However, there has been described that it is essential for the above-mentioned pyrrolo [2,3-d]pyrimidine derivatives to have a non-substituted amino group at the C2 position. (U.S. patent application Ser. No. 07/326,901).

Currently, it has been especially expected of cancer therapy to develop and create drug substances which can work through a novel mechanism of action to exhibit highly selective toxicity against cancer cells and also to achieve excellently improved therapeutic effect. MTX, an anti-tumor agent that can act basically through a mechanism to serve the antagonism against folic acid, is presently put into extensive clinical use but because of its relatively strong toxicity and inadequate efficacy against solid cancers, has failed to attain adequately satisfactory therapeutic effect.

In view of the above situations, the present inventors conducted repeatedly intensive research and as a result, found that the novel condensed heterocyclic compounds, inhibiting not less than one of the biosynthetic pathways in which folic acid and its related compounds are involved, can exhibit highly selective toxicity against various types of tumor cells and also produce excellent anti-tumor effect. This finding has led to completion of this invention. Namely, this invention is concerned with:

(1) Compounds as represented by the general formula (I):

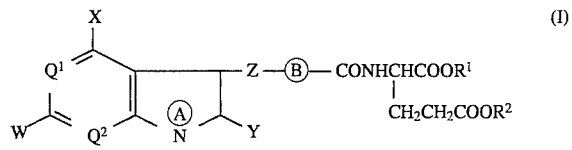

wherein the ring Ⓐ is a pyrrole ring which may be hydrogenated; —Ⓑ— is a divalent cyclic or chain group which may be substituted; one of $Q^1$ and $Q^2$ is N, with the other being N or CH; W is a halogen or hydrogen atom or a group bonded to the bonding line with a carbon, nitrogen, oxygen or sulfur atom, provided that W is not —NH$_2$; X is an amino, hydroxyl or mercapto group; Y is a hydrogen atom or a hydroxyl or amino group; Z is a straight-chain divalent group having a number of atoms of 2 to 5 composed of carbon atoms which each may be substituted, or carbon atoms which each may be substituted and one hetero atom which may be substituted; —COOR$^1$ and —COOR$^2$ each is the same as or different from the other and represents a carboxyl group which may be esterified, or its salt;

(2) A method for producing a compound according to claim 1, which comprises reacting a compound represented by the general formula:

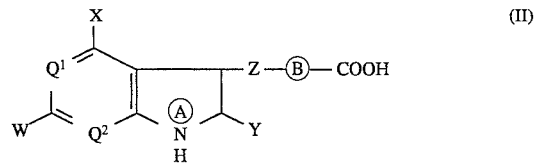

wherein the ring A is a pyrrole ring which may be hydrogenated; —B— is a divalent cyclic or chain group which may be substituted; one of $Q^1$ and $Q^2$ is N, with the other being N or CH; W is a hydrogen or halogen atom or a group bonded to the bonding line with a carbon, nitrogen, oxygen or sulfur atom, provided that W is not —NH$_2$; X is an amino, hydroxyl or mercapto group; Y is a hydrogen atom or a hydroxyl or amino group; Z is is a straight-chain divalent group having a number of atoms of 2 to 5 composed of carbon atoms which each may be substituted, or carbon atoms which each may be substituted and one hetero atom which may be substituted, or its rective derivative in respect to the carboxyl group with a compound represented by the general formula:

wherein —COOR$^1$ and —COOR$^2$ each is the same as or different from the other and represents a carboxyl group which may be esterified;

(3) An anti-tumor composition which comprises a compound according to claim 1 or its salt and a pharmaceutically acceptable carrier; and (4) A compound represented by the general formula:

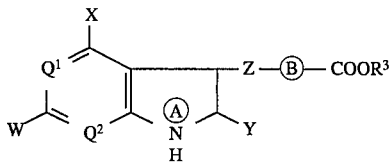

(IV)

wherein the ring Ⓐ is a pyrrole ring which may be hydrogenated; —Ⓑ— is a divalent cyclic or chain group which may be substituted; one of $Q^1$ and $Q^2$ is N, with the other being N or CH; W is a halogen or hydrogen atom or a group bonded to the bonding line with a carbon, nitrogen, oxygen or sulfur atom, provided that W is not —$NH_2$; X is an amino, hydroxyl or mercapto group; Y is a hydrogen atom or a hydroxyl or amino group; Z is a straight-chain divalent group having a number of atoms of 2 to 5 composed of carbon atoms which each may be substituted, or carbon atoms which each may be substituted and one hereto atom which may be substituted; —$COOR^3$ is a carboxyl group which may be esterified, or its salt.

In the case where, in the above formulae, $Q^1$ is N and X is a hydroxyl or mecapto group, or in the case Y is a hydroxyl group or amino group, the compounds (I), (II) and (IV) can exist as an equilibrium mixture with their tautomeric isomers. Illustrated below are the partial structural formulae capable of undergoing tautomerism, with the equilibria among them being shown, as well.

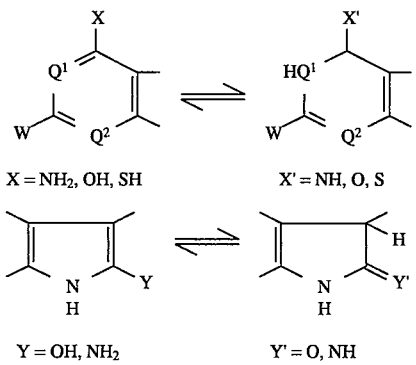

Throughout this specification, for the purpose of convenience of expression, the amino, hydroxyl and mercapto forms are to be described, with the corresponding designations being adopted, and in either case, their tautomers or the imino, oxo and thiooxo forms are understood to be included in the scope of this invention.

In the compounds (I) of this invention, furthermore, the presence of a plural number of asymmetric centers is possible, but except that the absolute configuration of the asymmetric carbon atom in the side chain derived from the glutamic acid moiety is S(L), the absolute configurations of other asymmetric centers may be either of S, R and a mixture of RS. In such a case, a plurality of diastereomers exist, and they can be easily separated by conventional separation and purification means, if necessary.

All the above-described diastereomers that can be separated by such procedures are included in the scope of this invention.

Referring to the above formulae, the pyrrole ring represented by the ring Ⓐ includes, for example, pyrrole and pyrroline rings.

Preferred examples of the cyclic radical in the divalent cyclic group which may be substituted, as represented by —Ⓑ—, include divalent five-membered or six-membered cyclic hydrocarbon or heterocylic groups which may have to three heteroatoms (e.g., N, O and S) contained therein, with their linkages or bonds desirably extending from the positions not mutually adjacent in the ring. As examples of the said divalent 5-membered cyclic hydrocarbon or hetero cyclic group represented by —Ⓑ—, there may be mentioned 1,3- or 3,5-cyclopentadiene-1,3-ylene, cyclopentene-(1,3, 1,4- or 3,5-)ylene, cyclopentane-1,3-ylene, thiophene-(2,4-, 2,5- or 3,4-)ylene, furan-(2,4-, 2,5- or 3,4-)ylene, pyrrole-(1,3-, 2,4-, 2,5- or 3,4-)ylene, thiazole-(2,4- or 2,5-)ylene, imidazole-(1,4-, 2,4- or 2,5-)ylene, thiazole-2,5-ylene, or their partially reduced forms or completely reduced forms, while examples of the said divalent six-membered cyclic hydrocarbon or heterocyclic groups include phenyl-(1,3- or 1,4-)ylene, cyclohexane-(1,3- or 1,4-)ylene, cyclohexene-(1,3-, 1,4, 1,5-, 3,5- or 3,6-)ylene, 1,3-cyclohexadiene-(1,3-, 1,4, 1,5-, 2,4-, 2,5- or 2,6-)ylene, 1,4-cyclohexadiene(1,3-, 1,4- or 1,5-)ylene, pyridine0(2,4-, 2,5-, 2,6- or 3,5-)ylene, pyran-(2,4-, 2,5-, 2,6-, 3,5-, 3,6- or 4,6-)ylene, pyrazine-(2,5- or 2,6-)ylene, pyridazine-3,5-ylene, or their partially reduced forms or completely reduced forms. Among them phenyl-1,4-ylene and thiophene-2,5-ylene ar particularly preferable examples as the divalent cyclic group of —Ⓑ—, The divalent chain groups which may be substituted, as represented by —Ⓑ—, preferably are divalent chain hydrocarbon groups of $C_2$ to $C_4$, and include, for example, $C_{2-4}$ alkylene, $C_{2-4}$ alkenylene $C_{2-4}$ alkynylene such as ethylene, ethenylene, ethynylene, trimethylene, propenylene, propynylene, propadienylne, tetramethylene, butenylene, butynylene or butanedienylene.

The divalent cyclic or lower chain group residue as represented by —Ⓑ— may have one or two substituents at its replacable positions. Examples of the said substituents include alkyl groups of $C_1$ to $C_3$ (e.g., methyl, ethyl, propyl, and isopropyl groups), alkenyl groups of $C_2$ to $C_3$ (e.g., vinyl, 1-methylvinyl, 1-propenyl, allyl and allenyl groups), alkynyl groups of $C_2$ to $C_3$ (e.g., ethynyl, 1-propenyl and propargyl groups), $C_{3-6}$ cycloalkeyl groups (e.g., cyclopropyl group), halogens (e.g, chlorine, bromine, fluorine, and iodine), hydroxyl, $C_{1-3}$ alkoxy (e.g., methoxy), di-$C_{1-3}$ alkylamino (e.g., dimethylamino), hologeno-$C_{1-3}$ alkyl (e.g., trifluoromethyl), oxo, $C_{1-3}$ acyl e.g., formyl), $C_{1-3}$ alkoxy-$C_{1-3}$ alkyl (e.g., methoxymethyl and 2-ethoxyethyl).

As the halogen atom represented by W, there may be mentioned fluorine, chlorine, bromine or iodine.

The group having carbon, nitrogen, oxygen or sulfur intervened therein, as represented by W, is not amino group but includes lower hydrocarbon groups, aryl groups, 5- or 6-membered heterocyclic groups, cyano group, carboxyl group, carbamoyl group, nitro group, hydroxyl group, alkoxy groups, allyloxy group, 5- or 6-membered heterocyclic-oxy groups, mercapto group, alkylthio groups, arylthio groups, 5- or 6-membered heterocyclic-thio groups, substituted amino groups, alkanoylamino groups, alloylamino groups, 5- or 6-membered carbonyl amino groups, alkanoyloxy groups, alloyloxy groups or 5or 6-membered heterocyclic-carbonyloxy groups.

When W represents a lower hydrocarbon group, its examples include alkyl groups of $C_1$ to $C_3$ (e.g., methyl, ethyl, propyl and isopropyl groups), alkenyl groups of $C_2$ to $C_3$ (e.g., vinyl, 1-methylvinyl, 1-propenyl, allyl, and allenyl groups), alkynyl groups of $C_2$ to $C_3$ (e.g., ethynyl, 1-propynyl and propargyl groups) and $C_{2-6}$ cycloalkyl groups (e.g., cyclopropyl group), and in cases where W is an aryl group, its examples include $C_{6-10}$ aryl such as phenyl or naphthyl groups, while in the cases of W representing 5- or 6-membered heterocyclic group, its examples include pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl, or their partially reduced forms or completely reduced forms, such as dioxoranyl,piperizino, morpholino, N-methylpiperazinyl, N-ethylpiperazinyl and dioxanyl. In cases where W represents lower hydrocarbon group, aryl groups and 5- or 6-membered heterocyclic groups, they may have one to two substituents, whereby such substituents include, for example, alkyl groups of $C_1$ to $C_3$ (e.g., methyl, ethyl, propyl and isopropyl groups), alkenyl groups of $C_2$ to $C_3$ (e.g, vinyl, 1-methylvinyl, 1-propenyl, allyl and allenyl groups), alkynyl groups of $C_2$ to $C_3$ (e.g., ethynyl, 1-propynyl and propargyl groups) or $C_{3-6}$ cycloalkyl groups (e.g., cyclopropyl group), as well as hylogen (e.g., fluorine), hydroxyl, oxo, $C_{1-3}$ alkylamino group (e.g., methoxy), di-$C_{1-3}$ alkylamino group (e.g., dimethylamino diethylamino), halogen-$C_{1-3}$ alkyl group (e.g., trifluoromethyl), $C_{1-3}$ acly group (e.g., formyl), hydroxy-$C_{1-4}$ alkyl group (e.g., hydroxymethyl, 2-hydroxyethyl), $C_{1-4}$ alkoxy-$C_{1-4}$ alkyl group (e.g., methoxymethyl and 2-ethoxyethyl.)

When W represents alkoxy, alkylthio, alkanoylamino and alkanoyloxy groups, their alkyl moieties include, as such, $C_{1-3}$ alkyl group as exemplified above in the case of W representing a lower hydrocarbon group, and in cases where W is aryloxy, arylthio, aroylamino and aroyloxy groups, the aryl radical in such groups includes, for example, $C_{6-10}$ aryl group such as phenyl or naphthyl groups. When W is 5- or 6-membered heterocyclic-oxy, 5- or 6-membered heterocyclicthio, 5- or 6-membered heterocyclic-carbonylamino or 5- or 6-membered heterocyclic-oxycarbonyl groups, furthermore, the 5- or 6-membered heterocyclic moieties in such groups include, as such, those as illustrated above in detail in the case of W representing 5- or 6-membered heterocyclic groups.

When W is a substituted amino group, its examples include mono-substituted and di-substituted amino groups, whereupon such substituted moieties include, as such, those as exemplified above in the case of W being the lower hydrocarbon group, aryl and 5- or 6-membered heterocyclic groups.

The carboxyl group which may be esterified, as represented by —COOR$^1$, —COOR$^2$ and —COOR$^3$, include for example carboxyl groups being esterified with lower alkyl groups of $C_1$ to $C_5$, benzyl groups which may be substituted (e.g., nitro, $C_{1-4}$ alkoxy) or phenyl groups which may be substituent. As the said lower alkyl groups, there may be mentioned, for example, methyl, ethyl, propyl, isopropyl, n-butyl, iso-butyl, sec-butyl, tert-butyl, n-pentyl, isopentyl, secpentyl, neo-pentyl and tert-pentyl, and the said benzyl which may have a substituent include for example benzyl, nitrobenzyl and methoxybenzyl, while the said phenyl which may have a substituent includes for example phenyl, nitrophenyl and methoxyphenyl.

In the divalent chain group having a number of atoms of 2 to 5 composed of carbon atoms which may be substituted or carbon atoms which may be substituted and one heteroatom (nitrogen, oxygen or sulfur atom) which may be substituted as represented by Z, the group composed of carbon atoms to be employed includes, for example, $C_{2-5}$ alkylene groups such as ethylene, trimethylene, tetra-methylene and pentamethylene, $C_{2-5}$ alkenylene groups such as vinylene, propenylene, 1- or 2-butenylene, butadienylene, 1- or 2-pentenylene, and 1,3- or 1,4-pentadienylene, and $C_{2-5}$ alkynylene groups such as ethynylene, 1- or 2-propynylene, 1- or 2-butynylene, and 1-, 2- or 3-pentynylene, while the group composed of carbon atoms which may be substituted and one heteroatom which may be substituted (nitrogen, oxygen or sulfur atom) ot be employed includes, for example, groups represented by the formula —Z$^1$—Z$^2$—Z$^3$— [wherein Z$^1$ and Z$^3$ each is the same as or different from the other and represents a bond or a divalent $C_{1-4}$ hydrocarbon group which may be substituted, provided that Z$^1$+Z$^3$ have one to four of carbon atoms; Z$^2$ is —O— or a group of the formula —S(O)$_n$— (wherein n is an integer of 0 to 2) or the formula

group (wherein R$^4$ is a hydrogen atom or a lower hydrocarbon group which may be substituted)]. As the divalent $C_{1-4}$ hydrocarbon group which may be substituted, as represented by Z$^1$ and Z$^3$, there may be used, for example, $C_{1-4}$ alkylene groups such as methylene, ethylene, trimethylene and tetramethylene, $C_{2-4}$ alkenylene groups such as vinylene, propenylene, 1- or 2-butenylene and butadienylene, and $C_{2-4}$ alkynylene groups such as ethynylene, 1- or 2-propynylene and 1- or 2-butynylene, while the lower hydrocarbon group which may be substituted, as represented R$^4$, includes for example alkyl groups of $C_1$ to $C_3$ (e.g., methyl, ethyl, propyl and isopropyl groups), alkenyl groups of $C_2$ to $C_3$ (e.g., vinyl, 1-methylvinyl, 1-propenyl, allyl and allenyl groups), alkynyl groups of $C_2$ to $C_3$ (e.g., ethynyl, 1-propynyl and propargyl groups) and $C_{3-6}$ cycloalkyl (e.g., cycloalkyl group). Carbon or/and hereto atom or atoms constitute the groups Z, hydrocarbon group represented by Z$^1$, Z$^2$ and R$^4$ may have one to two substituents, whereby the said substituents include, for example, alkyl groups of $C_1$ to $C_3$ (e.g., methyl, ethyl, propyl and isopropyl groups), alkenyl groups of $C_2$ to $C_3$ (e.g., vinyl, 1-methylvinyl, 1-propenyl, allyl and allenyl groups), alkynyl groups of $C_2$ to $C_3$ (e.g., ethynyl, 1-propynyl and propargyl groups) or $C_{3-6}$ cycloalkyl group (e.g., cyclopropyl group), as well as halogen (e.g., fluorine), hydroxyl, oxo, $C_{1-4}$ alkoxy group (e.g., methoxy), di-$C_{1-4}$ alkylamino group (e.g., dimethylamino, diethylamino), halogeno-$C_{1-4}$ alkyl group (e.g., trifluoromethyl), $C_{1-3}$ acyl group (e.g., formyl), hydroxy-C-$_{1-4}$ alky group (e.g., hydroxymethyl, 2hydroxyethyl), $C_{1-4}$ alkoxy-$C_{1-4}$ alkyl group (e.g., methoxymethyl and 2-ethoxyethyl.)

Below described is the process for producing the compounds (I) of this invention or their salts.

The compounds (I) or their salts can be obtained by acylating a glutamic acid deerivative as represented by the formula (III) with a carboxylic acid represented by the formula (II) or its reactive derivative in regard to the carboxyl group. The above-mentioned acylating means includes, for example, a procedure of acylating the compound (III) with the compound (II) or its reactive derivative in the presence of carbodiimides, diphenylphosphoric azide or diethyl cyanophosphate. The used amount of the compound (III) usually is in the range of about 1 to 20 mole equivalents against the compound (II) or its reactive derivative, preferably about 1 to 5 mole equivalents. The carbodiimides may be used ordinarily at a ratio of about 1 to 25 mole equivalents, preferably about 1 to 5 mole equivalents.

As the said carbodiimides, dicyclocarbodiimide is desirable from the standpoint of practical use, and in addition to this, there may be utilized other carbodiimides, such as diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-diethylaminopropyl)carbodiimide. the said acylation reaction is preferably carried out in the presence of an appropriate solvent, and as the solvent, use is made for example of water, alcohols (e.g., methanol and ethanol), ethers (e.g., dimethyl ether, diethyl ether, tetrahydrofuran. dioxane, monoglyme and diglyme), nitriles (e.g., acetonitrile), esters (e.g., ethyl acetate), halogenated hydrocarbons (e.g., dichloromethane, chloroform and carbon tetrachloride), aromatic hdyrocarbons (e.g., benzene, toluene and xylene), acetone, nitromethane, pyridine, dimethylsulfoxide, dimethylformamide, hexamethylphosphoramide, sulfolane or suitable solvent mixtures thereof. This reaction can be conducted by allowing the reaction to proceed in a solvent at a pH in the range of about 2 to 14, preferably about 6 to 9 and at a reaction temperature in the region of about −10° C. to the boiling point (up to about 100° C.) of the used reaction solvent, preferably about 0° to 50° C., for about 1 to 100 hours. The pH value of the reaction solution is suitably adjusted, for example with acids (e.g., hydrochloric acid, sulfuric acid, phosphoric acid, nitric acid and acetic acid), bases (e.g., sodium methylate, sodium ethylate, sodium hydroxide, potassium hydroxide, barium hydroxide, lithium hydroxide, sodium carbonate, potassium carbonate, barium carbonate, calcium carbonate, sodium hydrogencarbonate, trimethylamine, triethylamine, triethanolamine and pyridine) or buffers (e.g., phosphate buffer, borate buffer and acetate buffer), if necessary. This reaction can be allowed to proceed more advantageously by utilizing catalysts capable of accelerating the reaction. Such catalysts include, for example, base catalysts and acid catalysts. As the said base catalysts, there may be mentioned for example tertiary amines (e.g., aliphatic tertiary amines, such as triethylamine; aromatic tertiary amines, such as pyridine, alpha, beta- or gamma-picoline, 2,6-lutidine, 4-dimethylaminopyridine, 4-(1-pyrrolidinyl)pyridine, dimethylaniline and diethylaniline), while the acid catalysts include, for example, Lewis acids (e.g., anhydrous zin chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride, and boron trifluoride etherate). Among the above-cited catalysts, in many cases, 4-dimethylaminopyridine or 4-(1-pyrrolidinyl)pyridine is preferred. The used amount of the catalysts desirably is in the neighborhood of the catalytic quantities which can permit the acceleration to be accelerated, and normally ranges from about 0.01 to 10 mole equivalents against the compound (II), preferably from about 0.1 to 1 mole equivalent. The reactive derivatives of the carboxylic acids (II) in regard to the carboxylic group include, for example, derivatives of the compounds (II), such as their acid halides (e.g., fluorides, chlorides, bromides and iodides), their acid anhydrides (e.g., iodo-acetic anhydrides and isobutyric anhydrides), thief mixed acid anhydrides with lower mono-alkyl carbonates (e.g., monomethyl carbonate, monoethyl carbonate, monopropyl carbonate, monoisopropyl carbonate, monobutyl carbonate, monoisobutyl carbonate, mono-sec-butyl carbonate and mono-tert-butyl carbonate), their mixed-acid anhydrides with active esters (e.g., cyanomethyl esters, ethoxycarbonylmethyl esters, methoxymethyl esters, phenyl esters, o-nitrophenyl esters, p-nitrophenyl esters, p-carbomethoxyphenyl esters, p-cyanophenyl esters and phenylthio esters), their acid azides, their mixed-acid anhydrides with phosphoric acid esters (e.g., dimethyl phosphate, diethyl phosphate, dibenzyl phosphate and diphenyl phosphate) and their mixed-acid anhydrides with phosphorous acid esters (e.g., dimethyl phosphite, diethyl phosphite, dibenzyl phosphite and diphenyl phosphite). In the acylation means with use of such reactive derivatives, the reaction conditions such as the solvent, catalyst and reaction temperature, are the same as described previously in the case of acylation being carried out in the presence of carbodiimides the same as described previously in the case of acylation being carried out in the presence of carbodiimides.

In producing the compound (1-1), or its salt, of the formula (I) where —$COOR^1$ and —$COOR^2$ both are a carboxyl group, it is desirable to react the compound of the formula (II) where —$COOR^1$ and —$COOR^2$ both is an esterified carboxyl group with the compound (II) or its reactive derivative in regard to the carboxyl group, followed by the per se known decomposition or catalytic reduction reaction to conduct deesterification. The said decomposition reaction includes, for example, a hydrolysis reaction under basic conditions (Method A), a hydrolysis reaction under acid conditions (Method B-1) and a decomposition reaction under acid, nonaqueous conditions (Method B-2). Examples of the base which can be used in the Method A include metal alkoxides, such as sodium methoxide, sodium ethoxide, sodium butoxide and potassium butoxide, metal hydroxides, such as sodium hydroxide, potassium hydroxide, lithium hydroxide and barium hydroxide, and amines, such as ammonia, triethylamine and pyridine, and as the acid being usable in the Method B-1, there may be mentioned mineral acids, such as hydrochloric acid, hydrobroci acid, sulfuric acid, nitric acid and phosphoric acid, and organic acids, such as trifluoroacetic acid, trichloroacetic acid, methanesulfonic acid, benzenesulfonic acid, p-toluenesulfonic acid and camphorsulfonic acid, while the acid (catalyst) being utilizable in the Method B-2 includes, for example, mineral acids, such as hydrochloric acid, hydrobromic acid, perchloric acid, sulfuric acid, nitric acid and phosphoric acid, organic acids, such as trifluoroacetic acid, trichloroacetic acid, methansuflonic acid, benzenesulfonic acid, p-toluenesulfonic acid and camphorsulfonmmic acid, and Lewis acids, such as anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride and boron trifluoride etherate. Any of the decomposition reaction is carried out in an appropriate solvent at a temperature in the range of 0° C. to the boiling point of the used solvent, preferably 10° to 80° C. for 30 min to 2 days. Referring to the reaction solvent, usable in the case of the Methods A and B-1 are for example water, methanol, ethanol, propanol, butanol, ethylene glycol, methoxyethanol, ethoxyethanol, tetrahydrofuran, dioxane, monoglyme, diglyme, pyridine, dimethylformamide, dimethylsulfoxide, dulfolane or suitable solvent mixtures thereof, whereas in the case of the Method B-2, there are utilized for example ethyl acetate, dimethyl ether, diethyl ether, tetrahydrofuran, dioxane, monoglyme, diglyme, dichloromethane, chloroform, carbon tetrachloride, acetonitrile, benzene, toluene, xylene, nitromethane, pyridine or suitable solvent mixtures thereof. The said catalytic reduction reaction (Method C) is carried out in a suitable solvent at a temperature in the range of about −40° C. to the boiling point of the used solvent, more preferably about 0° to 50° C. The usable solvent includes, for example, water, alcohols (e.g., methanol, ethanol, propanol, isopropanol, butyl alcohol, sec-butyl alcohol, tert-butyl alcohol, ethylene glycol, methoxyethanol and ethoxyethanol), acetates (e.g., methyl acetate and ethyl acetate), ethers (e.g., dimethyl ether, diethyl ether, tetrahydrofuran, dioxane, monoglyme and diglyme) anolile, aromatic hydrocarbons (e.g., benzene, toluene and xylene), pyridine, dimethylformamide and suitable solvent mixtures thereof. As the catalyst for the catalytic reduction, there may be used, for example, palladium, platinum, rhodium and Raney nickel. On the occasion of utilizing such catalysts, addition of minutes quantities of acetic acid, trifluoroacetic acid, hydrochloric acid, sulfuric acid, etc. can in some instances permit the reaction to proceed advantageously. As a reaction time, may be usually used 20 minutes to 30 hours. It depends upon the properties of —COOR$^1$ and —COOR$^2$ which reaction should be employed for the conversion to the compound (I-1); normally, the Method A or B-1 is applicable advantageously, when —COOR$^1$ and —COOR$^2$ are carboxyl groups esterified with methyl, ethyl, propyl, butyl, sec-butyl, phenyl or substituted phenyls, and the Method B-2 can be applied favorably in the case of —COOR$^1$ and —COOR$^2$ being carboxyl groups esterified with isopropyl or tert-butyl group, whereas the Method B-1 or C is utilizable advantageously in the case of —COOR$^1$ and —COOR$^2$ being carboxyl groups esterified with benzyl or substituted benzyl groups. In cases where —COOR$^1$ and —COOR$^2$ each is different from the other, the above-mentioned Methods A, B-1, B-2 and C may be suitably combined.

Described in the following is the procedure of producing the starting compound (in the formula (II): $Q^1= Q^2=N$):

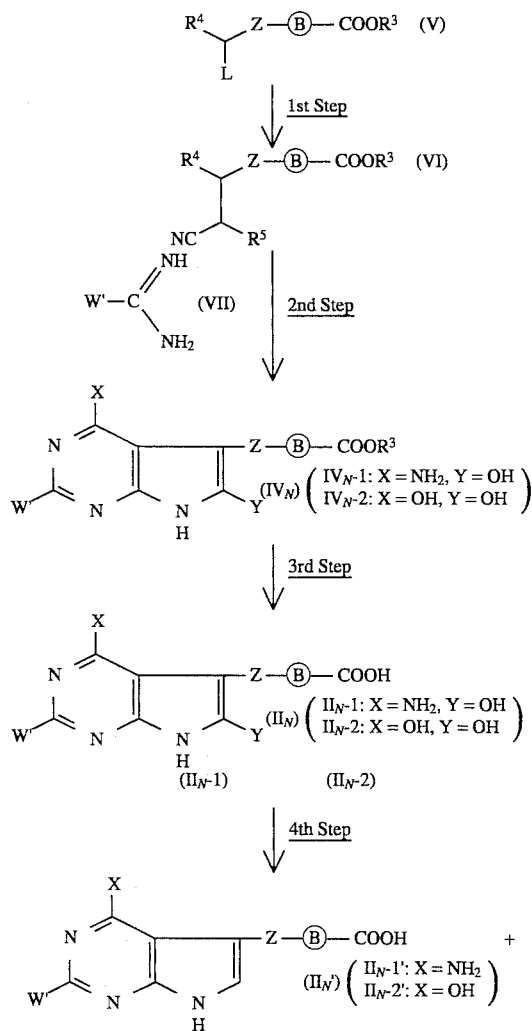

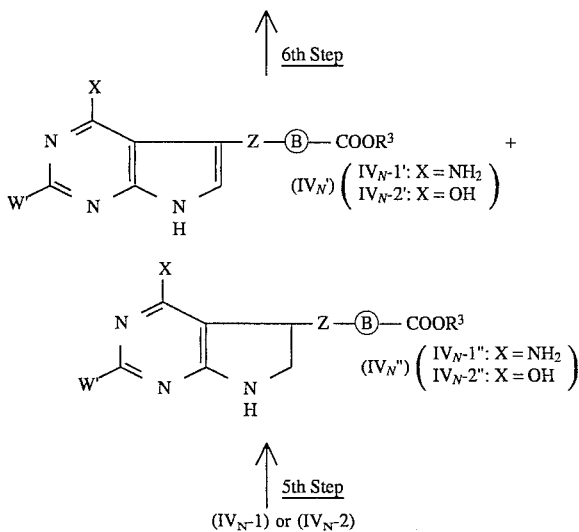

In the above steps, —(B)—, R$^3$, X, Y and Z are as defined hereinbefore; W' is a group as defined by W, such as a hydrogen atom, a hydrocarbon residue or a 5- or 6-membered heterocyclic, hydroxyl, alkoxy, aryloxy, 5- or 6-membered heterocyclic-oxy, mercapto, alkylthio, aryltuio, 5- or 6-membered heterocyclic-thio, substituted amino, alkanoylamino, aroyloxyamino or 5- or 6-membered heterocyclic carbonylamino group; R$^4$ is an esterified carboxyl group as represented by —COOR$^6$; R$^5$ is a cyano group or an ester;tried carboxyl group as represented by —COOR$^6$; and, L is a halogen atom (e.g., chlorine, bromine and iodine atoms) or an easily removable group (e.g., methanesulfonyloxy, benzenesulfonyloxy, p-toluenesulfonyloxy and trifluoromethanesulfonyloxy groups). The group R$^6$ in the esterified carboxyl group represented by the formula —COOR$^6$ includes, for example, lower alkyls (e.g., methyl, ethyl, propyl isopropyl, butyl, sec-butyl and tert-butyl), benzyl and substituted benzyls (e.g., p-nitrobenzyl and p-methoxybenzyl).

Given below is detailed description on the above reaction steps:

1st step:

The starting compound (V) can be converted to the compound (VI) by subjecting it to a condensation reaction with malononitrile or a cyanoacetate [NC—CH$_2$—COOR$^6$; R$^6$ is as defined hereinbefore] under basic conditions. With reference to the base, solvent reaction conditions, etc. to be employed, the procedures known per se can be adopted.

2nd step:

The compound (VI), with a compound represented by the general formula:

W'—C(NH$_2$)=NH  (VII)

[wherein W' is as defined hereinbefore] or its salt, allows reaction through its cyano or ester group of (VI) and then undergoes ring-closure cyclization to thereby form a pyrrolo [2,3-d]pyrimidine ring anew.

The acid salt of the compound (VII) includes, for example, its salts formed with mineral acids, such as hydrochloric acid, hydrobromic acid, hydroiodic acid, sulfuric acid, nitric acid, phosphoric acid and boric acid; and its salts formed with organic acids, such as oxalic acid, tartaric acid, lactic acid, citric acid, acetic acid, trifluoroacetic acid, methanesulfonic acid, ethanesulfonic acid, benzenesulfonic acid, p-toluenesulfonic acid and camphorsulfonic acid, while as the base salt of the compound (VII-1: W'=hydroxyl or mercapto group), there may be mentioned, for example, its salts formed with sodium, potassium, lithium, calcium, magnesium, aluminum, zinc, ammonium, trimethyl ammonium, triethyl ammonium, triethanol ammonium, pyridinium, substituted pyridinium, etc.

In the case of ring-closure, the reaction can in some instances be allowed to proceed advantageously under basic conditions. Examples of the usable base include metal alkoxides, such as sodium methoxide, sodium ethoxide and potassium tert-butoxide. The reaction solvent to be use includes, for example, methanol, ethanol, propanol, tert-butyl alcohol, dimethylsulfoxide and hexamethylphosphoramide, while the reaction temperature is 0° to 150° C., preferably 20° to 100° C., with the reaction time ranging from 1 to 48 hours.

3rd step:

The compound ($IV_N$-1: $X=NH_2$, $Y=OH$, or $IV_N$-2: $X=OH$, $Y=OH$) obtained in the 2nd step can have its ester residue [—$COOR^3$] undergo the same deesterification reaction as employed in the production of the compound (I-1) to thereby be converted to the compound ($II_N$-1: $X=NH_2$, $Y=OH$, or $II_N$-2: $X=OH$, $Y=OH$).

4th step:

The compound ($II_N$-1 or $II_N$-2) as obtained in the 3rd step can be subjected to a reduction reaction to produce the compound ($II_N$-1' and $II_N$-1"; $X=NH_2$, $Y=H$, or $II_N$-2' and $II_N$-2": $X=OH$, $Y=H$). The reduction reaction conditions are known per se, and, for example, the reduction reaction with metal hydrides (e.g., borane, allane or their art complexes) can be applied.

Also, the 3rd step and the 4th step can be carried out with the order of application being reversed. Namely, in the 5th step, the compound ($IV_N$-1 or $IV_N$-2) is treated through the same reduction reaction as conducted in the 4th step to give the compound ($IV_N$-1' or $IV_N$-1": $X=NH_2$, $Y=H$, or $IV_N$-2' and $IV_N$-2": $X=OH$, $Y=H$), which is then in the 6th step, subjected to the same deesterification reaction as employed in the 3rd step to produce the compound ($II_N$1' and $II_N$-1" or $II_N$-2' or $II_N$-2"). Which should be first carried out, the deesterification reaction or the reduction reaction, can be suitably decided depending for example upon the properties of the substitutes of the compound ($IV_N$-1 or $IV_N$-2).

The compound ($II_N$,) and ($IV_N$,) of the above-mentioned formulae ($II_N$) and ($IV_N$) where Y is hydrogen can be produced by means of the reaction steps to be shown in the following:

$$R^7-J^1-CH-CH-Z-\text{\textcircled{B}}-COOR^3 \quad (VIII)$$

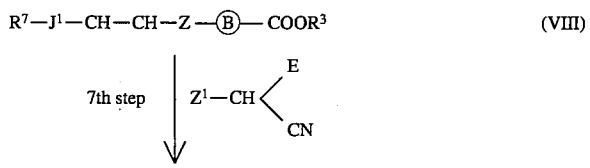

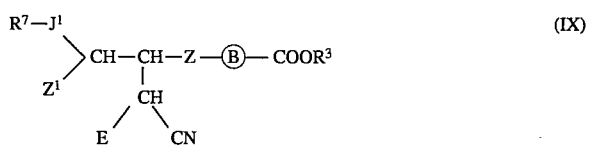

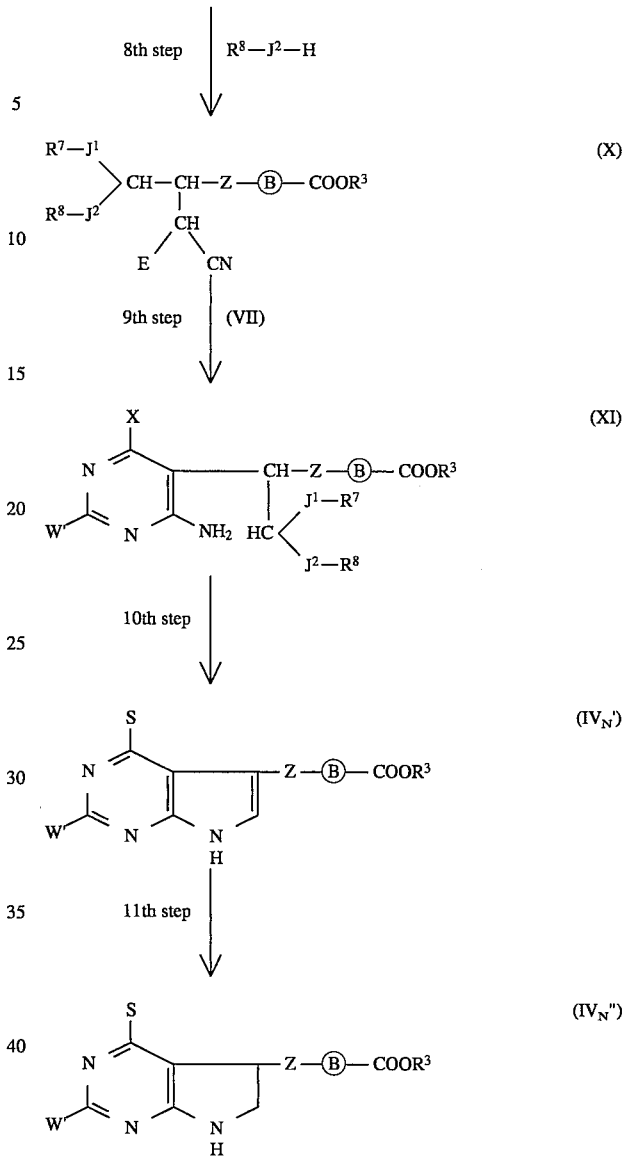

In the above reaction steps, —Ⓑ—, $R^3$, W', X and Z are as defined hereinbefore; $J^1$ and $J^2$ each is the same as or different from the other and represents oxygen or sulfur; $R^7$ and $R^8$ each is the same as or different from the other and represents a hydrocarbon group; $Z^1$ is a halogen atom (e.g., chlorine, bromine and iodine); E is a cyano group or a group represented by the formula —$COOR^9$, —$CSOR^9$ or —$CSSR^9$ ($R^9$ is a hydrocarbon group). Examples of the hydrocarbon group represented by $R^7$ and $R^8$ include lower alkyl groups of $C_1$ to $C_5$ (e.g., methyl, ethyl, propyl, isopropyl, n-butyl, isobutyl, sec-butyl, tert-butyl, n-pentyl, isopentyl, secpentyl, neo-pentyl and tert-pentyl), benzyl and phenyl groups. These lower alkyl, benzyl and phenyl groups may have one to three substituents. Such substituents include, for example, halogen atoms (e.g., fluorine, chlorine, bromine and iodine), nitro group, cyano group, alkoxy groups of $C_1$ to $C_4$ (e.g., methoxy, ethoxy, propoxy, isopropoxy, n-butoxy, isobutoxy, sec-butoxy and tert-butoxy groups), alkyl groups of $C_1$ to $C_4$ (e.g., methyl, ethyl, propyl, isopropyl, butyl, isobutyl, sec-butyl and tert-butyl groups), alkanoyl groups of $C_1$ to $C_4$ (e.g., formyl, acetyl, propionyl, n-butyryl and isobutyryl groups) and trifluoromethyl group.

The group $R^9$ in the formulae —COOR$^9$, —CSOR$^9$ and —CSSR$^9$ includes, for example, hydrocarbon group as described in detail for the groups $R^7$ and $R^8$.

Given below is detailed description on the above reaction steps:

7th step:

This is a step where

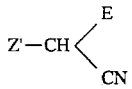

is allowed to undergo addition to the double bond ($R^7$—$J^1$—CH=CH—) in the compound (VIII) to give the compound (IX). The used amount of

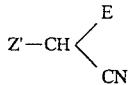

against the compound (VIII) generally is about 0.5 to 4 mole equivalents, preferably about 0.8 to 1.5 mole equivalents. This reaction is carried out in an appropriate solvent at a reaction temperature in the range of about −10° C. to the boiling point (up to about 100° C.) of the used solvent, preferably about 0° to 50° C. for about 30 min to 48 hours. As the solvent utilizable in the reaction, there are used, for example, alcohols (e.g., methanol and ethanol), ethers (e.g., dimethyl ether, diethyl ether, tetrahydrofuran, dioxane, monoglyme and diglyme), nitriles (e.g., acetonitrile), esters (e.g., ethyl acetate), halogenated hdyrocarbons (e.g., dichloromethane, chloroform and carbon tetrachloride), aromatic hydrocarbons (e.g., benzene, toluene and xylene) and suitable solvent mixtures thereof. In conducting the reaction, irradiation with light or addition of organic peroxides can in some instances permit the reaction to proceed advantageously. The said organic peroxides include, for example, t-butylhypochlorite, peracetic acid, perbenzoic acid and p-chloroperbenzoic acid. The compound (IX) as obtained by the above procedure is relatively reactive and may be isolated in this stage, although it can also be used directly in the following step without being isolated.

8th step:

The compound (IX) obtained in the 7th step can be reacted with alcohols; or thiols represented by $R^8$—$J^2$—H in an appropriate solvent at a reaction temperature in the range of about −10° C. to the boiling point (up to about 100° C.) of the used solvent, preferably about 0° to 50° C., for about 10 min to 24 hours to thereby produce the compound (X). As the solvent being utilizable in the reaction, there may be used, for example, ethers (e.g., dimethyl ether, diethyl ether, tetrahydrofuran, dioxane, monoglyme and diglyme), nitriles (e.g., acetonitrile), esters (e.g., ethyl acetate), halogenated hdyrocarbons (e.g., dichloromethane, chlorform and carbon tetrachloride), aromatic hydrocarbons (e.g., benzene, toluene and xylene) or suitable solvent mixtures thereof. The alcohols or thiols represented by $R^8$—$J^2$—H may be used in excess to utilize as a solvent.

9th step:

The compound (X), with a compound represented by the general formula (VII) in a suitable solvent, can allow reaction through its cyano, ester or thioester group of (X), and undergo cyclization, while it forms the pyrimidine ring, to thereby produce the compound (XI). This reaction can be carried out at a reaction temperature in the range of 0° to 150° C., preferably 20° to 80° C., for a reaction time in the region of 1 to 48 hours. The reaction, when conducted under basic conditions, can in some instances be allowed to proceed advantageously. The base being usable includes, for example, metal alkoxides, such as sodium methoxide, sodium ethoxide and potassium tert-butoxide. As the reaction solvent, there may be used, for example, methanol, ethanol, propanol, tert-butyl alcohol, dimethylsulfoxide, hexamethylphosphoramide or suitable solvent mixtures thereof.

10th step:

This step constitutes a reaction in which the group HC($J^1$—$R^7$)($J^2$—$R^8$) in the compound (IX) is restored to a carbonyl group, bringing about spotaneously an intra-molecular ring-closure reaction, to thereby be converted to the compound (IV$_N$'). The restoration reaction to a carbonyl group can be carried out by subjecting the compound (XI), as such or in a suitable reaction solvent, to a decomposition reaction at a reaction temperature in the range of about −10° to the boiling point (up to about 100° C.) of the used solvent, preferably about 0° to 50° C., for a period of time in the region of about 10 min to 100 hours. The said decomposition reaction includes, for example, a hydrolysis reaction under acidic conditions (Method B-1), decomposition reaction under acidic, non-aqueous conditions (Method B2), catalytic reduction reaction (Method C), decomposition reaction with use of metal salts (Method D) or decomposition reaction with oxidizing agents (Method E). The Methods B1, B-2 and C can be carried out by following, as such, the procedures as illustrated in detail for the decomposition reactions of the groups represented by the formulae —COOR$^1$ and —COOR$^2$. The metal salts ,which are usable in the Method D include, for example, cupric chloride, silver nitrate, silver oxide, mercuric chloride and tellurium salts (e.g., tellurium nitrate and tellurium trifluoroacetate), while the oxidizing agents which are utilizable in the Method E include, for example, oxygen-light, hydrogen peroxide, perbenzoic acid, m-chloroperbenzoic acid, perchlorates (e.g., lithium perchlorate, silver perchlorate, mercuric perchlorate and tetrabutylammonium perchlorate), nitrosylsulfuric acid, alkyl nitrites (e.g., isoamyl nitrite), iodine, bromine, chlorine, N-bromosuccinimide, sulfuryl chloride and chloramine T. Which method should be applied to restore a carbonyl group (C=O) can be suitably decided depending upon the chemical properties of —$J^1$—$R^7$ and —$J^2$—$R^8$. As the reaction solvent, there may be used, for example, water, alcohols (e.g., methanol, ethanol, propanol, isopropanol, butyl alcohol, sec-butyl alcohol, tert-butyl alcohol, ethylene glycol, methoxyethanol and ethoxyethanol), ethers (e.g., dimethyl ether, diethyl ether, tetrahydrofuran, dioxane, monoglyme and diglyme), aromatic hydrocarbons (e.g., benzene, toluene and xylene), halogenated hydrocarbons (e.g., dichloromethane, chloroform and carbon tetrahchloride), acetone, acetonitrile or suitable solvent mixtures thereof. The intramolecular ring-closure reaction in the step of producing the compound (IV$_N$') normally allows the amino group on the pyrimidine ring to condense spontaneously to the carbonyl group (C=O) in the course of or after restoration to thereby form a pyrrolo[2,3-d]pyrimidine ring. In conducting the reaction, the presence of acid catalysts can also permit the said ring-closure reaction to proceed quickly and in improved yields. The said acid catalysts include, for example, mineral acids, organic acids and Lewis acids as described in detail for the Methods B-1 and B-2.

11th step:

The compound (IV$_N$') having a pyrrole ring ring —Ⓐ—, as obtained in the 10th step, can be subjected to a catalytic reduction reaction as mentioned above in Method C, if necessary, to be converted easily to the compound (IV$_{N''}$) containing a pyrroline ring as Ⓐ.

In cases where —Ⓑ— is an alkenylene group or a phenylene group which has a substituent, such groups may be subjected to a catalytic reduction reaction in this step or either of the 1st to 10 th steps to thereby be converted to the corresponding cycloalkylene group. In carrying out the said catalytic reduction reaction, the previously mentioned Method C can be advantageously applied.

When W' is a hydroxyl, alkoxy, aryloxy, 5- or 6-membered heterocyclic-oxy, mercapto, alkylthio, arylthio, 5- or 6-membered heterocyclic-thio group, substituted amino, alkanoylamino, aroylamino or 5- or 6-membered heterocyclic carbonylamino group, such groups may be subjected to a per se known conversion reaction in this step or either suitable step of the 1st to 10th steps to thereby be converted to those groups as defined by W, such as a 5- or 6-membered heterocyclic group or halogen atom, or a cyano, carboxyl, carbamoyl, nitro, hydroxyl, alkoxy, aryloxy, 5- or 6-membered heterocyclic-oxy, mercapto, alkylthio, arylthio, 5- or 6membered heterocyclic-thio, substituted amino, alkanoylamino, aroylamino, 5- or 6-membered heterocyclic carbonylamino, alkanoyloxy, aroyloxy or 5- or 6-membered carbonyloxy group.

Also, the compound $(IV_{N'})$ or compound $(IB_{N'})$ can be subjected to the same deesterification reaction as mentioned in the 3rd step, if necessary, to be converted to the compound $(II_{N'})$ or compound $(II_{N''})$.

Described in the following is the process of producing the starting compound (in the formula (II), Y=H, and $Q^1=Q^2=N$ and $Q^2=CH$, or $Q^1=CH$ and $Q^2=N$).

The starting compound can be produced, for example, by means of the reaction steps to be shown in the following.

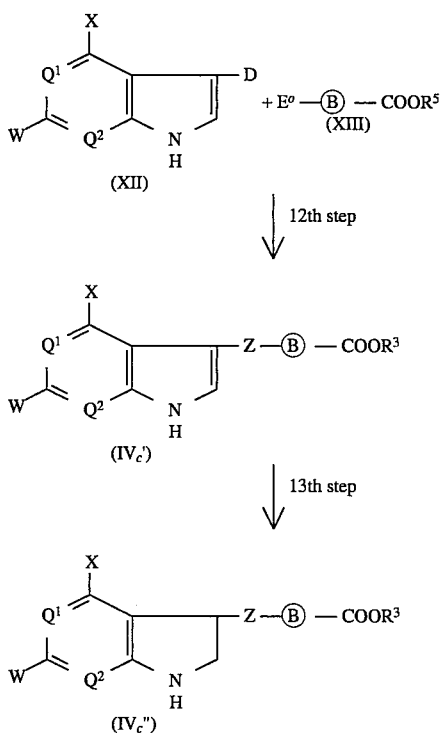

In the above formulae, —Ⓑ—, $R^3$, $Q^1$, $Q^2$, W and X are as defined hereinbefore, and the above reaction steps can permit the covalent bond to be formed between D and E to thereby produce a straight-chain divalent group having a number of atoms of 2 to 5, as represented by Z, being composed of carbon atoms which each may be substituted or carbon atoms and one heteroatom which may be substituted.

Referring to the synthetic method which permits formation of the covalent bond between the compound (XII) and compound (XIII), the compound (XII) and the compound (XIII) can be subjected to the so-called reaction causing the carbon-carbon bond, followed by a reduction reaction to thereby produce the compound $(IV_{c'})$, in the case of the group being composed of carbon atoms which each may have a substituent, for example, in cases where D is

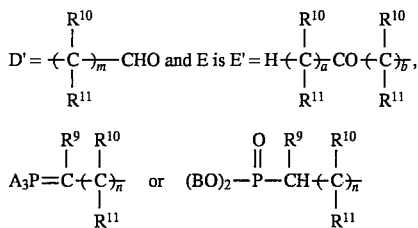

$D=E'$ and $E^o=D'$.

In the above formulae, $\underline{a}$, $\underline{b}$, $\underline{m}$, $\underline{n}$ ($=\underline{a}+\underline{b}$) and $\underline{m}+\underline{n}$ each is an integer in the range of 0 to 3; A is phenyl, butyl or cyclohexyl; B is ethyl or phenyl; $R^9$, $R^{10}$ and $R^{11}$, each being the same as or different from the other, represent a bonding linkage, a hydrogen atom or a substituent like the substituents in the lower hydrocarbon groups as described in detail for the groups, $Z^1$, $Z^2$ and $Z^4$, which each may be different from the other in the repeating units of $\underline{m}$ and $\underline{n}$.

In the case of Z being a group composed of $Z=—Z^1—Z^2—Z^3—$, for example, in cases where D is

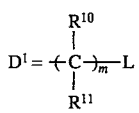

and $E^o$ is

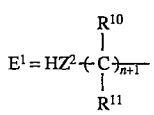

and, vice versa, $D=E^1$ and $E^o=D^1$, the so-called alkylation reaction is employed; when D is

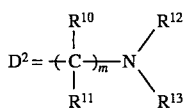

with $E^o$ being

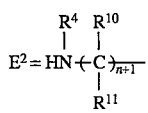

and, vice versa, $D=E^2$ and $E^o=D^2$, for example, the so-called amine exchange reaction (gramine-decomposition type of reaction) is advantageously used; and in cases where D is

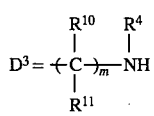

and $E^o$ is

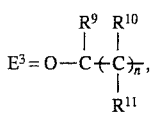

and, vice versa, $D=E^3$ and $E^o=D^3$, for example, use is made of a procedure which comprises allowing a Schiff base to be formed, followed by reduction or subjecting directly to a reductive alkylation reaction, if necessary.

In the above formulae, $\underline{m}$, $\underline{n}$, $\underline{m+n}$, L, $R^4$, $R^9$, $R^{10}$, $R^{11}$ and $Z^2$ are as defined hereinbefore; $R^{12}$ and $R^{13}$ each is the same or different from the other and represents hydrogen atom or a a hydrocarbon group which may be substituted, or $R^{12}$ and $R^{13}$ both may cooperate with the adjacent nitrogen atom to form a cyclic amino group which may be substituted. The hydrocarbon groups represented by $R^{12}$ and $R^{13}$ include, for example, alkyl groups of $C_1$ to $C_{18}$ (e.g., methyl, ethyl, propyl, isopropyl, butyl, isobutyl, sec-butyl, tert-butyl, pentyl, isopentyl, hexyl, isohexyl, heptyl,, octyl, nonyl, decyl, undecyl, dodecyl, ttradecyl, hexadecyl, octadecyl, 1,2-dimethylpropyl, 1-ethylpropyl, 1,2,2-trimethylpropyl, 1-propylbutyl and 2-ethylhexyl groups), alkenyl groups of $C_1$ to $C_{12}$ (e.g., vinyl, allyl, 1-methylvinyl, 2-methylvinyl, 1-octenyl and 1-decenyl groups), cycloalkyl groups of $C_3$ to $C_{12}$ (e.g., cyclopropyl, cyclobutyl, cyclopentyl, cyclohexyl, cycloheptyl, cyclooctyl and adamantyl groups), cycloalkenyl group of $C_3$ to $C_8$ (e.g., cyclopentenyl, cyclohexenyl, cycloheptenyl, cyclooctenyl, cyclopentadienyl, cycloexadienyl, cycloheptadienyl and cyclooctadienyl groups), aralkyl groups of $C_7$ to $C_{13}$ (e.g., benzyl, α-methylbenzyl, phenethyl and diphenylmethyl groups) and aryl groups of $C_6$ to $C_{10}$ (e.g., phenyl, α-naphthyl and β-naphthyl groups). Preferred examples of the cyclic amino group which $R^{12}$ and $R^{13}$ cooperate with the adjacent nitrogen atom to form include 4- to 10-membered rings, such as azetidinyl, pyrrolidinyl, pyrrolinyl, pyrrolyl, imidazolyl, pyrazolyl, imidazolinyl, piperidino, morpholino, dihydropyridyl, tetrahydropyridyl, N-methylpiperadinyl, N-ethylpiperazinyl, azacycloheptyl, azacyclooctyl, isoindolyl, indolyl, indolinyl, 2-iso-indolinyl, azacyclononyl and azacyclodecyl groups.

Such hydrocarbon groups as represented by $R^{12}$ and $R^{13}$ as well as such rings as formed by $R^{12}$ and $R^{13}$ in cooperation with the adjacent nitrogen atom may have one to two substituents. As the said substituent, there may be mentioned, for example, alkyl groups of $C_1$ to $C_4$ (e.g., methyl, ethyl, propyl, isopropyl, butyl, isobutyl, sec-butyl and tert-butyl groups)alkoxy groups of about $C_1$ to $C_4$ (e.g., methoxy, ethopxy, propoxy, isopropoxy, n-butoxy, iso-butoxy, sec-butoxy and tert-butoxy groups), alkanoyl groups of about $C_1$ to $C_4$ (e.g., formyl, acetyl, propionyl, n-butyryl and iso-butyryl groups), alkanoyloxy groups of about $C_1$ to $C_4$ (e.g., formyloxy, acetyloxy, propionyloxy, n-butyryloxy and iso-butyryloxy groups), carboxyl group, alkoxycarbonyl groups (e.g., methoxycarbonyl, ethoxycarbonyl, n-propoxycarbonyl, iso-propoxycarbonyl, n-butoxycarbonyl, isobutoxycarbonyl and tert-butoxycarbonyl groups), halogen atoms (e.g., fluorine, chlorine, bromine and iodine), hydroxyl group, nitro group, cyano group, triluforoemthyl group, amino group, mono-substituted amino groups (e.g., mmethyl-amino, ethylamino, propylamino, isopropylamino and butylamino groups), disubstituted amino groups (e.g., dimethylamino, diethylamino, dipropylamino, diisopropylamino and dibutylamino groups), alkanoylamido groups (e.g., formamido, acetamido, trifluoroacetamido, propionylamido, butrylamido and isobutyrylamido groups), carbamoyl group, N-substituted carbamoyl groups (e.g., N-methylcarbamoyl, N-ethylcarbamoyl, N-propylcarbamoyl, N-isopropylcarbamoyl and N-butylcarbamoyl groups), N,N-disubstituted carbamoyl groups (e.g., N,N-dimethylcarbamoyl, N,N,-diethylcarbamoyl, N,N-dipropylcarbamoyl, N,N-dibutylcarbamoyl, 1-atiridinylcarbonyl, 1azetidinylcarbonyl, 1-pyrrolidinylcarbonyl, 1-piperidinylcarnbonyl, N-methylpiperadinylcarbonyl and morpholinocarbonyl groups), carbamoylamino group, N-substituted carbamoylamino groups (e.g., N-methylcarbamoylamino, N-ethylcarbamoylamino, N-propylcarbamoylamino, N-isopropylcarbamoylamino and N-butylcarbamoylamino groups), N,N-disubstituted carbamoylamino groups (e.g., N,N-disubstituted carbamoylamino groups (e.g., N,N-diemthylcarbamoylamino, N,N-diethylaminocarbamoyl, N,N-dipropylaminocarbamoyl, N,Ndibutylaminocarbamoyl, 1-atilidinylcarbamoylamino, 1-azetidinylcarbonylamino, 1-pyrrolidinylcarbonylamino, 1-piperidinylcarbonylamino, N-methylpiperadinylcarbonylamino, and morpholinocarbonylamino groups), mercapto group, sulfo group, sulfino group, sulfono group, sulfamoyl group, N-substituted sulfamoyl groups (e.g., N-methylsulfamoyl, Nethylsulfamoyl, N-propyl sulfamoyl, N-isopropylsulfamoyl and N-butylsulfamoyl groups), N,N-disubstituted sulfamoyl groups (e.g., dimethylsulfamoyl, N,N-diethylsulfamoyl, N,Ndipropylsulfamoyl, N,N -dibutylsulfmoyl, 1-pyrrolidinylsulfonyl, 1-piperadinylsulfonyl and morpholinosulfonyl groups), alkylthio groups of about $C_1$ to $C_4$ (e.g., methylthio, ethylthio, propylthio, isopropylthio, n-butylthio, sec-butylthio and tert-butylthio groups), alkylsulfinyl groups of about $C_1$ to $C_4$ (e.g., methylsulfinyl, ethylsulfinyl, propylsulfinyl and butylsulfinyl groups) and alkylsulfonyl groups of about $C_1$ to $C_4$ (e.g., methylsulfonyl, ethylsulfonyl, propylsulfonyl and butylsulfonyl groups).

Below given is the detailed description on the 12th step:

For the condensation reaction through the formation of the carbon-carbon bonding, the known reactions (e.g., aldol reaction, Reformatsky reaction and Wittig reaction) are employable, while as the reduction reaction, normally, there is advantageously used the previously mentioned catalytic reduction reaction (Method C). When the aldol reaction is employed as a condensation reaction, the base catalyst which is usable includes, for example, metal hydroxides, such as sodium hydroxide, potassium hydroxide, lithium hydroxide and barium hydroxide, metal alkoxides, such as sodium methoxide, sodium ethoxide and potassium tert-butoxide, metal amides, such as sodium amide and lithium diisopropylamide, metal hydrides, such as sodium hydride and potassium hydride, organic metal compounds, such as phenyllithium and butyrllithium, and amines, such as triethylamine, pyridine, α-, β- or γ-picoline, 2,6-lutidine, 4-dimethylaminopyridine, 4-(1-pyrrolidinyl)pyridine, dimethylaniline and diethylaniline, while as the acid catalyst, there are mentioned for example mineral acids, such as hydrochloric acid, sulfuric acid, nitric acid, phosphoric acid and boric acid, and organic acids, such as oxalic acid, tartaric acid, acetic acid, trifluoroacetic acid, methanesulfonic acid, benzenesulfonic acid, p-toluenesulfonic acid and camphorsulfonic acid. According to the known procedure (Ei-Ichi Negishi, "Organometallics in Organic Synthesis", vol. 1, John Wiley & sons, New York, Chichester, Brisbane, Tronto), the ketone form is derived into the silyl enol ether form, which is then subjected to a condensation reaction with an aldehyde or its equivalent in the presence of Lewis acid (e.g., anhydrous zinc chloride, anhydrous aluminum chloride ($AlCl_3$), anhydrous ferric chloride, titanium chloride ($TiCl_4$), stannic chloride ($SnCl_4$), antimony pentachloride, cobalt chloride, cupric chloride and boron trifluoride etherate), or the ketone form can be treated with metal trifurate (e.g., dialkylboron trifurate and tin (II) trifurate) and amines (e.g., triethyl-amine, pyridine, α-, β- or γ-picoline, 2,6-lutidine, 4-dimethylaminopyridine, 4-(1-pyrrolidinyl)pyridine, dimethylaniline and diethylaniline) to convert into the enolate, followed by a condensation reaction with an aldehyde or its equivalent. The condensation reaction can be carried out in an appropriate solvent at a temperature in the range of −100° C. to the boiling point of the used solvent, preferably −78° to 100° C., for 1 min to 3 days. As the solvent, there may be used, for example, water, liquid ammonia, alcohols (e.g., methanol, ethanol, propanol, isopropanol, butyl alcohol, sec-butyl alcohol, tert-butyl alcohol, ethylene glycol, methoxyethanol and ethoxyethanol), ethers (e.g., dimethyl ether, diethyl ether, tetrahydrofuran, dioxane, monoglyme and diglyme)halogenated hydrocarbons (e.g., dichloromethane, chloroform and carbon tetrachloride), aliphatic hydrocarbons (e.g., pentane, hexane and heptane), aromatic hdyrocarbons (e.g., benzene, toluene and xylene), dimethylformamide, dimethylsulfoxide, hexamethylphosphor-amide, sulfolane and suitable solvent mixtures thereof. When Wittig reaction is used as a condensation reaction, the reagent which is usable includes, for example, metal hyroxides, such as sodium hydroxide, potassium hydroxide, lithium hydroxide and barium hydroxide, metal alkoxides, such as sodium methoxide, sodium ethoxide and potassium tert-butoxide, metal amides, such as sodium amide and lithium diisopropylamide, metal hyrides, such as sodium hydride and potassium hydride, organic metal compounds, such as phenyllithium and butyllithium, and amines, such as triethylamine, pyridine, α, β- or γ-picoline, 2,6-lutidine, 4-dimethylaminopyridine, 4-(1-pyrrolidinyl)pyrdine, dimethylaniline and diethylaniline. The reaction is carried out in an appropriate solvent at a temperature in the range of −20° C. to the boiling point of the used solvent, preferably 0° to 150° C., for 1 min to 10 days. As the reaction solvent, there may be used, for example, liquid ammonia, alcohols (e.g., methanol, ethanol, propanol, isopropanol, butyl alcohol, sec-butyl alcohol, tert-butyl alcohol, ethylene glycol, methoxyethanol and ethoxyethanol), ethers (e.g., dimethyl ether, diethyl ether, tetrahydrofuran, dioxane, monoglyme and diglyme), aliphatic hydrocarbons (e.g., pentane, hexane and heptane), aromatic hdyrocarbons (e.g., benzene toluene and xylene), dimethylformamide, dimethylsulfoxide, hexamethylphosphoramide, sulfolane and suitable solvent mixtures thereof.

Furthermore, Reformatsky reaction can be employed to perform condensation. Referring to the reaction conditions of Reformatsky reaction, the reagent being usable includes for example zinc, magnesium, aluminum and tin, and the reaction itself is conducted in an appropriate solvent at a temperature in the range of −20° C. to the boiling point of the used solvent, preferably 0° to 150° C., for 30 min to 3 days. As the reaction solvent, there may be employed, for example, ethers (e.g., dimethyl ether, diethyl ether, tetrahydrofuran, dioxane, monoglyme and diglyme), aliphatic hydrocarbons (e.g., pentane, hexane and heptane), aromatic hdyrocarbons (e.g., benzenes, toluene and xylene) and suitable solvent mixtures thereof.

The alkylation reaction or amine exchange reaction can be carried out by allowing the compound (XII) and Compound (XIII), as such or in an appropriate solvent, to undergo reaction at a temperature in the range of about −10° C. to the boiling point of the used reaction solvent, preferably about 10° to 80° C., for about 10 min to 48 hours. The Compound (XIII) is used at a ratio of about 1 to 50 moles against mole of of the Compound (XII), more preferably about 1 to 10 moles. As the reaction solvent, there are used, for example, water, alcohols (e.g., methanol, ethanol, propanol, isopropanol, butyl alcohol, sec-butyl alcohol, tert-butyl alcohol, ethylene glycol, methoxyethanol and ethoxyethanol), ethers (e.g., diethyl ether, tetrahydrofuran, dioxane, monoglyme and diglyme), halogenated hydrocarbons (e.g., dichloromethane, chloroform and carbon tetrachloride), nitriles (e.g., acetonitrile), aliphatic hydrocarbons (e.g., pentane, hexane, heptane and octane), cyclic aliphatic hdyrocarbons (e.g., cyclopentane and cyclohexane), aromatic hdyrocarbons (e.g., benzene, toluene and xylene), nitromethane, pyridine, dimethylformamide, dimethylsulfoxide, hexamethylphosphoramide, sulfolane and suitable solvent mixtures thereof. Also, it in some instances is desirable to carry out the reaction in the presence of base, if necessary. The base being usable includes, for example, the bases to be utilized in Wittig reaction. When a phase-transfer catalyst (e.g., cetyltrimethylammonium chloride) is used at a ratio in the range of 0.01 to 0.2 equivalent, preferably 0.02 to 0.05 equivalent, against the Compound (XII) or Compound (XIII), furthermore, the reaction can be allowed to proceed advantageously, as well. In the case of the amine exchange reaction, the reaction can in some instances be allowed to proceed under milder conditions, when the Compound (XII) is for example converted into salts with methyl bromide, methyl iodide, methyl methanesulfonate, methyl benzenesulfonate, methyl p-toluenesulfonate, etc.

The above-mentioned reaction causing the Schiff base to be formed is conducted by allowing the Compound (XII) and Compound (XIII), as such or in an appropriate solvent, to undergo reaction at the molar ratio of (XII)/(XIII)= about 10 to 0.1 at a temperature in the range of −10° C. to the boiling point of the used reaction solvent for about 10 min to 48 hours. In this reaction, the Compounds (XII) and (XIII) after having its aldehyde or ketone moiety protected in the form of acetal or ketal may be used. As the reaction solvent, nonaqueous solvents are desirable, and there may be used, for example, alcohols (e.g., methanol, ethanol, propanol, isopropanol, butyl alcohol, sec-butyl alcohol, tert-butyl alcohol, ethylene glycol, methoxyethanol and ethoxyethanol), ethers (e.g., dimethyl ether, diethyl ether, tetrahydrofuran, dioxane, monoglyme and diglyme), esters (e.g., methyl acetate and ethyl acetate), halogenated hydrocarbons (e.g., dichloro-methane, chloroform and carbon tetrachloride), nitriles (e.g., acetonitrile), aliphatic hydrocarbons (e.g., pentane, hexane, heptane and octane), cyclic aliphatic hdyrocarbons (e.g., cyclopentane and cyclohexane), aromatic hydrocarbons (e.g., benzene, toluene and xylene), acetone, nitromethane, pyridine, dimethylformamide, dimethylsulfoxide, hexamethylphosphoramide, sulfolane and suitable solvent mixtures thereof. As the dehydrating agent, for example, molecular sieves, calcium chloride, magnesium sulfate, sodium sulfate and calcium sulfate can be added, or a pH value of the reaction solution can be adjusted suitably with acids (e.g., hydrochloric acid, hydrobromic acid, hydroiodic acid, sulfuric acid, nitric acid and phosphoric acid), bases (e.g., metal hydroxides, such as sodium hydroxide, potassium hydroxide, lithium hydroxide and barium hydroxide, sodium methoxide, sodium ethoxide, potassium tert-butoxide, sodium carbonate, potassium carbonate, barium carbonate, calcium carbonate, sodium hydrogencarbonate, trimethylamine, triethylamine, triethanolamine and pyridine) or buffers (e.g., phosphate buffers, borate buffers and acetate buffers) to thereby enhance the reaction rate and yields. The reduction reaction and reductive alkylation reaction of the Schiff base are carried out through hydride reduction or catalytic reduction in an appropriate solvent at a reaction temperature in the range of about −40° C. to the boiling point of the used solvent, more preferably about 0° to 50° C. As the solvent being usable, there are used the reaction solvents to be utilized in the alkylation reaction or amine exchange reaction as described previously, as well as acetates (e.g., are carried out through hydride reduction or catalytic reduction in an appropriate solvent at a reaction temperature in the range of about −40° C. to the boiling point of the used solvent, more preferably about 0° to 50° C. As the solvent being usable, there are used the same reaction solvents as utilized in the alkylation reaction or amine exchange reaction as described above, as well as acetates (e.g., methyl acetate and ethyl acetate). As the catalytic reduction reaction, the previously mentioned Method C can be employed as such. The reagents which are used in the hydride reduction include, for example, lithium aluminum hydride, sodium borohydride, lithium borohydride and lithium cyanoborohydride, and the used amount of such reducing reagents is in the range of the equimolar to 100-fold molar quantity of the compound to be reduced, normally 2-fold to 20-fold the molar quantity.

When —$Z^2$— is

and $R^4$ is a hydrogen atom, the said group —HN—, in some instances, undergoes ring-closure with the position in the pyrrole ring to form a tricyclic compound (pyrrolo[3',2':4,5]pyrrolo[2,3-d]pyrimidine derivative). In such a case, the treatment with acids or bases can result easily in conversion into the objective bicyclic compound.

13th step:

As is the case with the 11th step, the ring A in the Compound (IVc') can be reduced to thereby produce the compound (Ivc").

Referring to the above-mentioned production methods, when —$Z^2$— is —S— (sulfur atom), the compound (I) of this invention can be subjected directly to the oxidation reaction or subjected to the oxidation reaction in either of the applicable arbitrary steps to thereby produce the compound having —$S(O)_n$— [n=1 or 2] as —$Z^2$—. The oxidation reaction can be carried out to produce the objective compound by allotting the compound to be oxidized to undergo reaction normally in an appropriate solvent under the presence of 0.3 to 3.0 equivalents against the compound of an oxidizing agent, preferably 0.5 to 2.5 equivalents, at a temperature of −10° to +100° C., preferably 0° to 50° C., for 10 min to 48 hours, desirably 30 min to 24 hours. Preferred examples of the oxidizing agent which is to be used in the reaction include peroxides (e.g., hydrogen peroxide, peracetic acid, perbenzoic acid and m-chloroperbenzoic acid). As the reaction solvent, there are used, for example, water, acetic acid, ketones (e.g., acetone and methyl ethyl ketone), ethers (e.g., dimethyl ether, diethyl ether, dioxane, monoglyme and diglyme), halogenated hydrocarbons (e.g., dichloro-methane, chloroform and carbon tetrachloride), aliphatic hydrocarbons (e.g., pentane, hexane, heptane and octane), cyclic aliphatic hydrocarbons (e.g., cyclopentane and cyclohexane), aromatic hydrocarbons (e.g., benzene, toluene and xylene) or suitable solvent mixtures thereof.

Furthermore, the amino, hydroxyl or mercapto group as represented by X in the Compounds (I), (II) and (IV) can be converted into one another, as the case may be, by means of substituent replacement reactions on the pyrimidine ring known in literature [supplement volume of "Tanpakushitsu/Kakusan/Kouso (Proteins/Nucleic Acids/Enzymes)" (1968)].

In addition, the reactions, reagents and reaction conditions as well as the protective groups to be applied for functional groups as used if necessary, which are to be carried out or employed in the 1st step through 13th step or in the step of producing the starting compound, are already known and described in detail in the following literature [J. F. W. McOmine, "Protective Groups in Organic Chemistry", Plenum Press, London and New York ( 1973)], [Pine, Hendrickson and Hammond, "Organic Chemistry" (4th edition), [I] to [II], Hirokawa Shoten of Japan] and [M. Fieser and L. Fieser, "Reagents for Organic Synthesis", vol. 1 to 13, Wiley Interscience, New York, London, Sydney and Tronto (1969–1988)].

The intermediates for the compounds of this invention as well as the compounds (I) of this invention, or their salts, that are produced by means of the above mentioned procedures, can be isolated from the reaction mixtures by the conventional separation means, such as concentration, solvent extraction, chromatography and recrystallization.

The compounds (I), (II) and (IV) obtainable by the production method of this invention may form salts. Examples of the salts with bases include salts formed with alkali metals, alkaline earth metals, non-toxic metals, ammoniums and substituted ammoniums, such as sodium, potassium, lithium, calcium, magnesium, aluminum, zinc, ammonium, trimethylammonium, triethylammonium, triethanolammonium, pyridinium and substituted pyridinium. The salts with acids include, for example, salts formed with mineral acids, such as hydrochloric acid, sulfuric acid, nitric acid, phosphoric acid and boric acid, and salts formed with organic acids, such as oxalic acid, tartaric acid, acetic acid, trifluro-acetic acid, methanesulfonic acid, benzenesulfonic acid, p-toluenesulfonic acid and camphorsulfonic acid.

The compounds (I) of this invention and thief pharmaceutically or biologically acceptable salts exhibit inhibitory activity against not less than one kind of the enzymes utilizing folic acid and its related compounds as a substrate. Consequently, these compounds can be used either alone or in combination with other antitumor agents for the purpose of treatment of choriocarcinoma, leukemia, breast adenocarcinoma, head and neck cancer (epithelioma), squamocarcinoma, cellule lung cancer and lymphosarcoma as well as other various tumors.

The Compounds (I) or their salts, when intended to be used as an antitumor agent, can be administered orally or parenterally, as such or after being processed into such dosage forms as powder, granule, tablet, capsule, suppository and injectable solution by means of the conventional procedures with use of pharmacologically allowable carriers, excipients, diluents, etc. Their dosage amount varies depending upon the species of subject animals (warm-blooded animals such as human, dog, cat, rabbit, monkey, rat, mouse, etc.), type of disease, severity of symptoms, kind of compounds, route of administration, etc., and their daily dose for the above warm-blooded animals is about 2.0 to 200, preferably 4.0 to 80 mg/kg body weight as the Compound of this invention in the case of oral administration, while the daily dose ranges from about 1.0 to 100, preferably 2.0 to 40 mg/kg in the case of parenteral administration. The method of administration for injectable solutions includes, for example, intramuscular injection, intrperitoneal injection, subcutaneous injection and intravenous injection.

The above mentioned procedures of processing into pharmaceutical preparations are conducted into practice in accordance with the per se known methods. In manufacturing the above-described oral preparations, for example, tablets, binders (e.g., hydroxypropylcellulose, hydroxypropyl methylcellulose and macrogoal), disintegrating agents (e.g., starch and carboxymethylcellulose calcium), lubricants (e.g., magnesium stearate and talc) and others can suitably be formulated.

In producing such non-oral, parenteral pharmaceutical preparations as injectable solution, tonicity agents (e.g., glucose, D-sorbitol, D-mannitol and sodiumchloride), preservatives (e.g., benzyl alcohol, chlorobutanol, methyl p-oxybenzoate and propyl p-oxybenzoate),buffering agents (e.g., phosphate buffers and sodium acetate buffers) and others can be suitably incorporated.

With reference to a specific example of the manufacture of of tablets, for example, about 1.0 to 50 mg of the Compound (1) or a salt thereof of this invention, 100 to 500 mg of lactose, about 50 to 100 mg of corn starch and about 5 to 20 mg of hydroxy-propylcellulose, being weighed out for use in the manufacture of one tablet, are mixed, granulated and admixed with corn starch and magnesium stearate, followed by compression into a tablet weighing about about 100 to 500 mg and measuring about 3 to 10 mm in diameter, in accordance with the conventional procedures. The resulting tblet can furthermore be processed into an enteric-coated tablet by providing coating with use of a ca. 5 to 10% solution of hydroxypropylmethylcellulose phthalate (about 10 to 20 mg per tablet) and castor oil (about 0.5 to 2.0 mg per tablet) in acetone-ethanol mixture. Referring to a specific example of producing injectable solutions, for example, about 2.0 to 50 mg of sodium salt of the Compound (I) of this invention, as weighed out for use in the preparation of one ampoule, (I) is dissolved in about 2 ml of isotonic saline, and the solution is filled into an ampoule, followed by fusion and heat sterilization at about 110° C. for about 30 min, or (II) is dissolved in a solution of about 10 to 40 mg of mannitol or sorbitol in about 2 ml of sterilized distilled water and the solution is filled into an ampoule, followed by lyophilization and fusion to thereby prepare injectable solution. On the occasion of the use of the lyophilized compound, the said ampoule is opened, and the compound can be dissolved for example in istonic saline to a concentration of about 1.0 to 25 mg/ml to prepare injectable solution intended for use in the subcutaneous, intravenous or intramuscular administration.

REFERENCE EXAMPLE 1

Production of tert-butyl 5-formyl-2-thiophenecarboxylate:

5-Formyl-2-thiophenecarboxylic acid (12.3 g) and tert-butyl alcohol. (58.38 g) were dissolved in dichloromethane (150 ml), and a solution of dicyclohexyl carbodiimide (19.49 g) in dichloromethane (50 ml) and a solution of 4-dimethylaminopyridine (0.96 g) in dichloromethane (10 ml) were added to the solution, followed by stirring at room temperature for 16 hours. The precipitate, which separated out, was filtered out, and the filtrate was concentrated to dryness. The resulting residue was purified by flush column chromatography (300 g of silica gel; ethyl acetate-hexane= 1:99 5:95) to give the subject compound (11.76 g).

IR (KBr): 2990, 2810, 1710, 1680, 1365, 1290, 1220, 1160, 1030 cm$^{-1}$. $^1$H-NMR (CDCl$_3$) δ: 1.59(9H, s), 7.71(1H, d, J=4 Hz), 7.76(1H, d, J=4 Hz), 9.96(1H, s)

REFERENCE EXAMPLE 2

Production of tert-butyl 5-(4-hydroxy-1-butenyl)-2-thiophenecarboxylate:

(3-Hydroxypropyl)triphenylphosphonium bromide (10.04 g) was added to a tetrahydrofuran suspension (60 ml) of sodium hydride (0.6 g) under a stream of argon, followed by heating under reflux for 4 hours. A tetrahydrofuran solution (20 ml) of the compound (5.31 g) as obtained in Reference Example 1 was added to the mixture, followed by heating under reflux for 2 hours. After the solvent was distilled off under reduced pressure, the residue was treated with added ether (150 ml), and the resulting insoluble matter was filtered out in the presence of cellite. The filtrate was concentrated under reduced pressure, and the residue was purified by flush column chromatography (280 g of silica gel; hexane-ethyl acetate= 10:1 4:1 ) to give the subject compound (5.46 g).

IR (Neat): 3400, 2980, 1700, 1520, 1440, 1365, 1290, 1245, 1160, 1090, 1040 cm$^{-1}$. $^1$H-NMR (CDCl$_3$) δ: 1.57(9H, s), 2.47(0.8H, q, J=6.2 Hz), 2.72(1.2 Hz, dq, J=6.6 Hz, 1.8 Hz), 3.72–3.88(2H, m), 5.77(0.6H, dt, J=11.4 Hz, 7.6 Hz), 6.20(0.4H, dt, J=14 Hz, 7.6 Hz), 6.58(0.4H, d, J=15.8 Hz), 6.33(0.6H, d, J=11.6 Hz), 6.86(0.4H, d, J=3.6 Hz), 6.95(0.6H, d, J=3.6 Hz), 7.55(0.4H, d, J=3.6 Hz), 7.61(0.6H, d, J=3.6 Hz).

REFERENCE EXAMPLE 3

Production of tert-butyl 5-(4-hydroxybutyl)-2-thiophenecarboxylate:

The compound (5.46 g) as obtained in Reference Example 2 was dissolved in ethanol (100 ml), and after 10% palladium-carbon (5.46 g) was added, the mixture was stirred under hydrogen atmosphere for 1 hour. Using cellite, the catalyst was filtered out, and the filtrate was concentrated under reduced pressure to give the subject compound (5.25 g).

IR (Neat): 3400, 2940, 1710, 1540, 1460, 1370, 1295, 1165, 1095 cm$^{-1}$. $^1$H-NMR (CDCl$_3$) δ: 1.56(9H, s), 1.59–1.66(2H, m), 1.70–1.85 (2H, m), 2.86(2H, t, J=7.4 Hz), 3.67(2H, t, J=6 Hz), 6.76(1H, d, J=3.6 Hz), 7.54(1H, d, J=3.6 Hz).

REFERENCE EXAMPLE 4

Production of tert-butyl 5-(4-oxobutyl)-2-thiophenecarboxylate:

A dichloromethane solution (10 ml) of dimethylsulfoxide (3.81 g) was added to a dichloromethane solution (30.9 ml) of oxalyl chloride (3.09 g) at −60° C., followed by stirring for 2 min. A dichloromethane solution (20 ml) of the compound (5.2 g) as obtained in Reference Example 3 was added to the reaction solution at the same temperature, followed by stirring for 15 min, and triethylamine (10.27 g) was added dropwise to the mixture, followed by stirring for 5 min. After the reaction temperature was raised to 0° C. over the 30 min period, the reaction solution was poured into water (250 ml), and the mixture was extracted with dichloromethane. The extract was concentrated under reduced pressure, and the resulting residue was purified by flush column chromatography (100 go silica gel; ethyl acetate-hexane=3:97 5:95) to give the subject compound (4.19 g).

IR (Neat): 2980, 2940, 1730, 1700, 1460, 1370, 1300, 1280, 1170, 1110 cm$^{-1}$. $^1$H-NMR (CDCl$_3$) δ: 1.57(9H, s), 2.02(2H, q, J=7.2 Hz), 2.52(2H, t, J=7.2 Hz), 2.87(2H, t, J=7.2 Hz), 6.76(1H, d, J=3.6 Hz), 7.55(1H, d, J=3.6 Hz)

REFERENCE EXAMPLE 5

Production of tert-butyl 5-(5-methoxy-4-pentenyl)-2-thiophenecarboxylate:

A 1-mole tetrahdyrofuran solution (21.8 ml) of potassium tert-butoxide was added to a toluene solution (25 ml) of (methoxymethyl)triphenylphosphonium chloride (7.48 g) at 0° C., followed by stirring for 10 min. A toluene solution (25 ml) of the compound (5.04 g) as obtained in Reference Example 4 was added dropwise to the solution mixture at the same temperature, followed by stirring at room temperature for 2 hours. Ether (150ml) was added to the reaction solution, and the organic layer was separated, then washed successively with water and saturated aqueous sodium chloride solution and dried over anhydrous sodium sulfate. The solvent was distilled off under reduced pressure, and the resulting residue was purified by flush column chromatography (100 g of silica gel; ethyl acetatehexane= 1:49) to give the subject compound (4.71 g).

IR (Neat): 2970, 2930, 1705, 1650, 1455, 1360, 1295, 1250, 1165, 1090 cm$^{-1}$. $^1$H-NMR (CDCl$_3$) δ: 56(9H, s), 1.73(2H, q, J=7.2 Hz), 1.94–2.18 (2H, m), 2.81(2H, t, J=7.2 Hz), 3.51(1.8 Hz, s), 3.59(1.2Hz, s), 4.33(0.4H, q, J=7.2 Hz), 4.70(0.6H, dt, J=7.2 Hz,12.8 Hz), 5.91 (0.4H, d, J=6 Hz), 6.29(0.6H, d, J=12.8 Hz), 6.74(1H, d, J=3.8 Hz), 7.54(1H, d, J=3.8 Hz).

REFERENCE EXAMPLE 6

Production of tert-butyl 5-[5,5-dicyano-4-(dimethoxymethyl)pentyl]-2-thiophenecarboxylate:

Bromomalononitrile (2.555 g) and the compound (4.15 g) as obtained in Reference Example 5 were dissolved in dichloromethane (82.5 ml) under argon atmosphere, and after molecular sieve 3A (2.1 g) was added, the reaction mixture was irradiated with ultraviolet ray for 2.5 hours, by use of a UV lamp for analytical use having a filter removed. Methanol (5.11 ml) was added to the reaction solution, followed by stirring for 15 min, and the solution mixture was poured into ice water containing a 2N aqueous potassium carbonate solution (18 ml), followed by extraction with dichloromethane. The extract layer was washed with water and dried over anhydrous sodium sulfate, and the solvent was distilled off under reduced pressure. The resulting residue was purified by flush column chromatography (100 g of silica gel; ethyl acetate-hexane=1:19 1:9) to give the subject compound (3.95 g).

IR (Neat): 2980, 2940, 2250, 1700, 1455, 1365, 1300, 1280, 1165, 1095 cm$^{-1}$. $^1$H-NMR (CDCl$_3$) δ: 1.56(9H, s), 1.68 to 1.97(4H, m), 2.21–2.33 (1H, s), 2.89(2H, t, J=7 Hz), 3.42(3H, s), 3.46(3H, s), 4.12(1H, d, J=4 Hz), 4.33(1H, d, J=5.2 Hz), 6.79(1H, d, J=3.6 Hz), 7.55(1H, d, J=3.6 Hz)

REFERENCE EXAMPLE 7

Production of tert-butyl 5-[4-(4,6-diaminopyrimidin-5-yl)-5,5-dimethoxypentyl]-2-thiophenecarboxylate Under argon atmosphere, formamidine acetate (200 mg) was suspended in tert-butyl alcohol (5 ml), a solution (1.92 ml) of 1-mole tetrahydrofuran solution of potassium butoxide was added thereto, and the mixture was stirred for 10 minutes. After adding a solution (7 ml) of the product compound (606 mg) of Reference Example 6 in tertbutyl alcohol thereto, the mixture was refluxed by heating for 3 hours. To the reaction mixture, further added formamidine acetate (200 mg) and 1-mole tetrahydrofuran solution (1.92 ml) of potassium tert-butoxide, and the mixture was refluxed by heating for 1 hour. The resulting reaction mixture was poured into ice water (100 ml), and extracted with dichloromethane. The organic layer was dried with anhydrous sodium sulfate, distilled under reduced pressure to remove solvent. The resultant residue was purified by flush column chromatography (carrier; 52.5 g of silica gel, developing solvent; dichloromethane-ethanol= 49:1–19:1) to give the subject compound (93 mg).

IR (KBr): 3470, 3320 , 3170, 2940, 1695, 1635, 1575, 1455, 1370, 1300, 1160, 1095, 840 cm$^{-1}$. $^1$H-NMR (CDCl$_3$) δ: 1.52–1.80(3H, m), 1.56(9H, s), 1.96–2.17(1H, m), 2.78 (2H, t, J=7.4 Hz), 2.88–2.97(1H, m), 3.49(3H, s), 3.54(3H, s ), 4.45(2H, d, J=3.2 Hz), 4.67(2H, brs), 5.30(2H, brs), 6.72(1H, d, J=3.6 Hz), 7.53(1H, d, J=3.6 Hz), 8.01 (1H, s)

EXAMPLE 1

Production of diethyl N-[5-[3-(4-amino-7H-pyrrolo[2,3-d]pyrimidin-5-yl)propyl]-2-thenoyl]-L-glutamate:

The compound (90 mg) as obtained in Reference Example 7 was dissolved in a mixed solution of trifluoroacetic acid (3 ml) and water (0.02 ml), followed by stirring at room temperature for 2 hours. The solvent was distilled off under reduced pressure, and the residue was dried under reduced pressure at 90° C. to produce quantitatively crude 5-[3-(4amino-7H-pyrrolo[2,3-d]pyrimidine-5-yl)propyl]-2-thio phenecarboxylic acid. The whole quantity of the product and diethyl L-glutamate hydrochloride (76.6 mg) were dissolved in dimethylformamide (2 ml), and a dimethylformamide solution (0.5 ml) of diethyl phosphorocyanidate (38.2 mg) and then a dimethylformamide solution (0.5 ml) of triethylamine (97 mg) were added dropwise to the solution at 0° C., successively. The reaction mixture was stirred at 0° C. for 30 min and then at room temperature for 3 hours, and the solvent was distilled off under reduced pressure. The resulting residue was purified by flush column chromatography (10 g of silica gel; dichloromethane separated from conc. aqueous ammonia 10% NH$_3$ containing ethanol:dichloromethane=1:29 1:19) to give the subject compound (85 mg).

IR (KBr): 3320, 3250, 2980, 1735, 1640, 1580, 1460, 1375, 1320, 1250, 1200, 1020, 805 cm$^{-1}$. $^1$H-NMR (CDCl$_3$) δ: 1.23(3H, t, J=7.6 Hz), 1.31(3H, t, J=7.6 Hz), 2.02–2.17(3H, m), 2.21–2.38(1H, m), 2.43–2.83(2H, m), 2.82 (2H, t, J=7.4 Hz), 2.95(2H, t, J=7.4 Hz), 4.13(2H, q, J=7 Hz), 4.24(2H, q, J=7 Hz), 4.69–4.80(1H, m), 5.13(2H, brs), 6.81(1H, d, J=3.3 Hz) , 6.89(1H, d, J=7.6 Hz) , 7.42(1H, d, J=3.8 Hz) , 8.28(1H, s), 9.27(1H, brs).

EXAMPLE 2

Production of N-[5-[3-(4-amino-7H-pyrrolo[2,3-d]pyrimidin-5-yl)propyl[-2-thenoyl] -L-glutamic acid:

The compound (83 mg) as obtained in Example 1 was dissolved in a mixed solution of tetrahydrofuran-water (1:1, 3 ml), and a 1N aqueous sodium hdyroxide solution (0.51 ml) was added to the solution, followed by stirring at room temperature for 1.5 hours. The solution was concentrated to a volume of about 1.5 ml under reduced pressure, and the resulting insoluble matter was filtered out through Millipore filter. The filtrate was admixed with acetic acid, and the resulting powder was filtered out, washed with water and dried under reduced pressure at 70° C. to give the subject compound (54 mg).

IR (KBr): 3400, 3120, 2950, 1725, 1670, 1620, 1545, 1450, 1400, 1320, 1260, 1200, 1165, 880 cm$^{-1}$. $^1$H-NMR (Me$_2$SO-d$_6$): 1.81–2.18(4H, m), 2.34(2H, t, J=7.6 Hz), 2.82(2H, t, J=7.6 Hz), 2.87( 2H, t, J=7.6 Hz), 4.29–4.41 (1H, m), 6.45(2H, s), 6.86(1H, s), 6.90(1H, d, J=3.6 Hz), 7.70(1H, d, J= 3.6 Hz), 7.99(1H, s), 8.50(1H, d, J=7.6 Hz), 11.25(1H, s).

REFERENCE EXAMPLE 8

Production of methyl 4-[4-(4,6-diamino-2-methylpyrimidin-5-yl)-5,5-dimethoxypentyl]benzoate Under argon atmosphere, 1-mole tetrehydrofuran solution (8.7 ml) of potassium tert-butoxide was added to a suspension (5 ml) of acetamidine hydrochloride (823 ml) in terbutyl alcohol and the mixture was stirred for 10 minutes. To the resultant mixture, a solution (8.7 ml) of methyl 4-[5,5-dicyano-4-(dimethoxymethyl)pentyl]benzoate (1.44 g) which is obtainable from methyl 4-formylbenzoate by the procedures of Reference Examples 2-6 in tert-butyl alcohol was added and refluxed by heating for 3 hours. The reaction mixture was poured into water (150 ml) and extracted with chloroform. The organic layer was dried with anhydrous sodium sulfate and distilled under reduced pressure to remove solvent. The resulting residue was purified by column chromatography [carrier; 70 g of silica gel, developer; chloroform: 8% aqueous ammonia containing ethanol=98:2] to give the subject compound (1.09 g).

IR (KBr): 3460, 3400, 3320, 3160, 2950, 1710, 1645, 1610, 1570, 1430, 1280, 1180, 1110, 1080, 960 cm$^{-1}$.
$^1$H-NMR (CDCl$_3$) δ: 1.45–1.77(3H, m), 1.96–2.13(1H, m), 2.32(3H, s), 2.63(2H, t, J=7.4 Hz), 2.86–2.97(1H, m), 3.46(3H, s), 3.51(3H, s), 3.90(3H, s), 4.41(1H, d, J=3.2 Hz), 4..52(2H, s), 5.24(2H, s), 7.19(2H, d, J=8.2 Hz), 7.93(2H, d, J=8.2 Hz)

EXAMPLE 3

Production of methyl 4-[3-(4-amino-2-methyl-7H-pyrrolo[2,3-d]pyrimidin-5-yl)propyl] benzoate 10% solution (2.68 ml) of hydrogen chloride in ether and water (0.02 ml) were added to a solution (2.68 ml) of the product compound (0.95 g) of Reference Example 8 in tetrahydrofuran-methyl alcohol (29:5.17 ml) and the mixture was stir red at room temperature for 3 hours. To the reaction mixture, water (10 ml) and conc. aqueous ammonia were added to make the mixture alkaline, and then tetrahydrofuran and methyl alcohol were remove from the mixture by distillation. Resulting precipitates were collected by filtration, washed with water, alcohol and ether in order, and dried to give the subject compound (0.753 g).

IR (KBr): 3490, 3300, 3100, 2940, 1720, 1645, 1610, 1580, 1480, 1460, 1435, 1310, 1280, 1180, 1110, 1020 cm$^{-1}$.
$^1$H-NMR (CDCl$_3$/CD$_3$OD) δ: 1.96–2.14(2H, m), 2.52(3H, s), 2.75(2H, t, 7.4 Hz) 3.92(3H, s), 6.74(1H, s), 7.28(2H, d, J=8.2 Hz), 7.98(2H, d, J=8.2 Hz)

REFERENCE EXAMPLE 9

Production of methyl 4-[4-(4,6-diamino-2-mercaptopyrimidin-5-yl)-5,5-dimethoxypentyl]benzoate Methyl 4-[5,5-dicyano-4-(dimethoxymethyl)pentyl]benzoate 5.78 g) and thiourea (1.33 g) were subjected to the same reaction as in Reference Example 8 to give the subject compound (2.21 g).

IR (KBr): 3350, 3180, 2950, 1720, 1630, 1610, 1565, 1510, 1440, 1390, 1285, 1120, 1060, 970 cm$^{-1}$. $^1$H-NMR (CDCl$_3$) δ: 1.45–1.95(4H, m), 2.61(2H, t, J=6.6 Hz), 2.76–2.87(1H, m), 3.44(3H, s), 3.50, s), 3.87(3H, s), 4.37(1H, d, J=2.6 Hz), 6.24(2H, s), 6.56(2H, s), 6.78(1H, s), 7.19(2H, d, J=8.4 Hz ), 7.91(2H, d, J=8.4 Hz)

REFERENCE EXAMPLE 10

Production of methyl 4-[4-(4,6-diaminopyrimidin-5-yl)-5,5-dimethoxypentyl]benzoate The product compound (0.6 g) of Reference Example 9 was dissolved in methyl alcohol (29.5 ml), Raney nickel was added thereto and the mixture was stirred vigorously at 70° C. for 3.5 hours. From the hot mixture, the catalyst was removed by filtration and solvent was removed by distillation under reduced pressure from the filtrate to give the subject compound (0.46 g).

IR (KBr): 3460, 3400, 3320, 3140, 2940, 1715, 1650, 1610, 1580, 1460, 1280, 1180, 1110, 1065, 960 cm$^{-1}$.
$^1$H-NMR (CDCl$_3$) δ: 1.46–1.79(3H, m), 1.95–2.17(1H, m), 2.63(2H, t, J=7 Hz), 2.81–3.01(1H, m), 3.48(3H, s), 3.52(3H, s), 3.90(3H, s), 4.43(1H, d, J=2.4 Hz), 4.66(2H, s), 5.27(2H, s), 7.19(2H, d, J=7.8 Hz), 7.93(2H, d, J=7.8 Hz), 8.01(1H, s)

EXAMPLE 4

Production of diethyl N-[4-3-(4-amino-2-methyl-7H-pyrrolo[2,3-d]pyrimidin-5-yl)propyl] benzoyl]-L-glutamate;

The product compound of Example 3 (325 mg) was dissolved in tetrahydrofuran-methyl alcohol (1:1.30 ml), 1N aqueous sodium hydroxide solution (2 ml) and water (3 ml) were added thereto and the mixture was stirred at room temperature for 15 hours. After neutralizing the mixture by adding 1N hydrochloride (2 ml) thereto, solvent was removed from the mixture by distillation and the resulting residue was dried at 90° C. under reduced pressure, thereby crude 4-[3-(4-amino-2-methyl-7H-pyrrolo[2,3-d]pyrimidin-5-yl)propyl]benzoic acid was obtained quantitatively. The whole amount of the crude compound and diethyl glutamate hydrochloride (350 mg) were dissolved in dimethylformamide (20 ml), a solution (1 ml) of diethyl cyanophosphate (172 mg) in dimethylformamide were added thereto at 0° C. and subsequently, at the same temperature, a solution (1 ml) of triethylamine (304 mg) in dimethyl-formamide was added dropwise thereto. The reaction mixture was stirred at 0° C. for 30 minutes and then at room temperature for 3 hours, and solvent was removed by distillation under reduced pressure from the mixture. The resulting residue was purified by column chromatography [carrier; 50 g of silica gel, developing solvent; dichloromethane separated from conc. aqueous ammonia—ethanol containing 10% NH$_3$: chloroform= 2:98] to give the subject compound (351 mg) as white crystals IR KBr): 3300, 3120, 2980, 2930, 1740, 1640, 1615, 1575, 1540, 1460, 1310, 1230, 1160, 1100, 1030, 970 cm$^{-1}$.
$^1$H-NMR (CDCl$_3$) δ: 1.31(3H, t, J=7.2 Hz), 1.35(3H, t, J=7.2 Hz), 1.98–2.50(6H, m), 2.56 (3H, s) , 2.75(2H, t, J=7.2 Hz), 4.12(2H, q, J=7.2 Hz), 4.76–4.87(1H, m), 5.09(2H, s), 6.76(1H, s), 7.06(1H, d, J=7 Hz), 7.77(2H, d, J=8.2 Hz), 9.80(1H, s)

EXAMPLE 5

Production of N-[4-[3-(4-amino-2-methyl-7H-pyrrolo[2,3-d]pyrimidin-5-yl)propyl] benzoyl]-L-glutamic acid The product compound (192 mg) of Example 4 was dissolved in a mixed solution (10 ml) of tetrahydrofuran—water (7:3). After adding 1N aqueous sodium hydroxide thereto, the solution was stirred at room temperature for 3 hours, concentrated the volume to 4 ml under reduced pressure and resulting insoluble materials were removed by filtration with millipore filter. Acetic acid (0.2 ml) was added to the filtrate, and resulting crystals were collected by filtration, washed with ice water, methanol and then ether, and dried at 70° C. under reduced pressure to give the subject compound (135 mg) as white crystals.

IR (KBr): 3490, 2950, 1675, 1640, 1540, 1505, 1450, 1400, 1300, 1260, 1100, 1020, 970 cm$^{-1}$. $^1$H-NMR (Me$_2$SO-d$_6$) δ: 1.77–2.19(4H, m), 2.33(3H, s), 2.35(2H, t, J=7.2 Hz), 2.72(2H, t, J=8 Hz), 2.77(2H, t, J=8 Hz), 4.32–4.46(1H, m), 6.36(2H, s), 6.76(1H, s), 7.31(2H, d, J=8.2 Hz), 7.81 (2H, d, J=8.2 Hz), 8.50(1H, d, J=7 Hz), 11.01(1H, s)

EXAMPLE 6

Production of methyl 4-[3-(4-amino-7H-pyrrolo[2,3-d]pyrimidin-5-yl)propyl]benzoate The product compound (0.44 g) of Reference Example 10 was subjected to the same reaction Reference Example 3, thereby the subject compound (0.28 g) was obtained.

IR (KBr): 3470, 3300, 3150, 3120, 2940, 1725, 1640, 2605, 1460, 1320, 1230, 1180, 1110, 1020 cm$^{-1}$. $^1$H-NMR (CDCl$_3$) δ: 2.0–2.15(2H, m), 2.79(2H, t, J=2 Hz), 2.80(2H, t, J=72. Hz), 3.91(3H, s), 5.16(2H, s), 6.86(1H, s), 7.29(2H, d, J=8.2 Hz), 7.99(2H, d, J=8.2 Hz), 8.28(1H, s), 10.19(1H, s)

EXAMPLE 7

Production of diethyl N-[4-[3-(4-amino-7H-pyrrolo[2,3-d]pyrimidin-5-yl)propyl)benzoyl]-L-glutamate The product compound (0.264 g) of Example 6 was subjected to the same reaction as Example 4 to condense with diethyl glutamate, thereby the subject compound (0.206 g) was obtained.

IR (KBr): 3300, 3150, 2980, 2930, 1740, 1640, 1620, 1600, 1580, 1540, 1470, 1375, 1255, 1200, 1100, 1020 cm$^{-1}$. $^1$H-NMR (CDCl$_3$) δ: 1.23(3H, t, J=7.2 Hz), 1.31 (3H, t, J=7.2 Hz), 1.98–2.39(4H, m), 2.42–2.55(2H, m), 2.77(2H, t, J=7.2 Hz), 2.80(2H, t, J=7.2 Hz), 2.80(2H, t, J=7.2 Hz), 4.12(2H, q, J=7.2 Hz), 4.25(2H, q, J=7.2 Hz), 4.76–4.86(1H, m), 5.13(2H, s), 6.83(1H, s), 7.08(1H, d, J=7.6 Hz), 7.28(2H, d, J=8.2 Hz), 7.77(2H,d,J=8.2Hz), 8.26(1H, s), 9.55(1H, s)

EXAMPLE 8

Production of N-[4-[3-(4-amino-7H-pyrrolo[2,3-d]pyrimidin-5-yl)propyl]benzoyl]-L-glutamic acid The product compound (0.118 g) of Example 7 was subjected to the same reaction as Example 5, thereby the subject compound (0.08 g) was obtained.

IR (KBr): 3400, 2940, 1670, 1640, 1540, 1510, 1400, 1335, 1255, 1190, 1100, 1020 cm$^{-1}$. $^1$H-NMR (Me$_2$SO-d$_6$) δ: 1.80–2.18(4H, m,), 2.35(2H, t, J=7.2 Hz), 2.73(2H, t, J=7.2 Hz), 2.79(2H, t, J=7.2 Hz), 4.34–4.46(1H, m), 6.39(2H, s), 6.85(1H, s), 7.32(2H, d, J=8.2 Hz), 7.81(2H, d, J=8.2 Hz), 7.99(1H, s), 8.47(1H, d, J=7.8 Hz), 11.22(1H, s)

EXAMPLE 9

Production of methyl 4-[3-(4-amino-2-mercapto-7H-pyrrolo[2,3-d]pyrimidin-5-yl)propyl] benzoate The product compound (0.18 g) of Reference Example 9 was subjected to the same reaction as Reference Example 3, thereby the subject compound (0.113 g) was obtained.

IR (KBr): 3490, 3400, 3320, 3200, 2950, 1720, 1620, 1600, 1570, 1535, 1440, 1285, 1110, 1020, 940 cm$^{-1}$. $^1$H-NMR (Me$_2$SO-d$_6$) δ: 1.75–1.94(2H, m), 2.71(2H, t, J=7.2 Hz), 2.75(2H, t, J=7.2 Hz), 3.83(3H, s), 6.65(2H, s), 6.73(1H, s), 7.34(2H, d, J=8.2 Hz), 7.87(2H, d, J=8.2 Hz), 11.33(1H, s)

EXAMPLE 10

Production of diethyl N-[4-[3-(4-amino-2-mercapto-7H-pyrrolo[2,3-d]pyrimidin-5-yl)propyl]benzoyl]-L-glutamate The product compound (72.3 mg) of Example 9 was subjected to the same reaction as Example 4 to condense with diethyl glutamate, thereby the subject compound (35 mg) was obtained.

IR (KBr): 3470, 3350, 3200, 2980, 1735, 1620, 1595, 1565, 1530, 1500, 1445, 1370, 1235, 1200, 1095, 1020, 940, 850 cm$^{-1}$. $^1$H-NMR (Me$_2$SO-d$_6$) δ: 1.16(3H, t, J=7.2 Hz), 1.19(3H, t, J=7.2 Hz), 1.75–1.96(2H, m), 1.97–2.20(2H, m), 2.43(2H, t, J=7.4 Hz), 2.62–2.83(4H, m), 4.0(2H, q, J=7.2 Hz), 4.10(2H, q, J=7.2 Hz), 4.35–4.50(1H, m), 6.66(2H, s), 6.73(1H, s), 7.29(2H, d, J=8.2 Hz), 7.79(2H, d, J=8.2 Hz), 8.63(1H, d, J=7.2 Hz), 41.34(1H, s)

EXAMPLE 11

Production of N-[4-[3-(4-amino-2-mercapto-7H-pyrrolo[2,3-d]pyrimidin-5-yl]propyl)benzoyl]-L-glutamic acid The product compound (30 mg) of Example 10 was subjected to the same reaction as Example 5, thereby the subject compound (19 mg) was obtained.

IR (KBr): 3350, 3200, 2930, 1710, 1620, 1570, 1535, 1500, 1450, 1400, 1240, 1190, 1100, 4020, 940 cm$^{-1}$. $^1$H-NMR (Me$_2$SO-d$_6$) δ: 1.77–2.20(4H, m), 2.35(2H, t, J=7.4 Hz), 2.64–2.85(4H, m), 4.33–4.47(1H, m), 6.65(2H, s), 6.73(1H, s), 6.73(1H, s), 7.29(2H, d, J=8.2 Hz), 7.80(2H, d, J=8.2 Hz), 8.51 (1H, d, J=7.4 Hz), 11.34(1H, s)

We claim:

1. A compound of the formula:

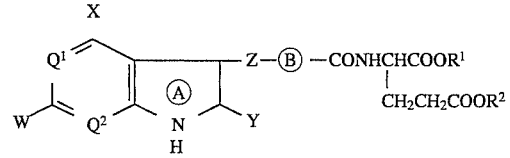

wherein the ring A is a pyrrole or pyrroline ring, B' is a thiophen-2,5-ylene or phenyl-1,4-ylene, W' is a hydrogen atom, a $C_{1-4}$ alkyl group or mercapto group, X is an amino group, hydroxyl group or mercapto group, Y is a hydrogen atom, $R^1$ and $R^2$ independently are a hydrogen atom, $C_{1-5}$ alkyl group, benzyl group which may be substituted with a nitro group or a methoxy group or phenyl group which may be substituted with a nitro group or a methoxy group and Z is —CH$_2$CH$_2$CH$_2$—, or its salt.

2. A compound according to claim 1, which is diethyl N-[5-3-(4-amino-7H-pyrrolo[2,3-d]pyrimidin-5-yl)propyl]-2-thenoyl]-glutamate.

3. A compound according to claim 1, which is N-[5-[3-(4-amino-7H-pyrrolo[2,3-d]pyrimidin-5 -yl]propyl)-2-thenoyl)L-glutamic acid.

4. A compound according to claim 1, which is diethyl N-[4-[3-(4-amino-2-methyl-7H-pyrrolo[2,3-d]pyrimidin-5-yl)propyl]propyl]benzoyl]-L-glutamate.

5. A compound according to claim 1, which is N-[4-[3-(4-amino-2-methyl-7H-pyrrolo[2,3-d] pyrimidin-5-yl)propyl]benzoyl]L-glutamic acid.

6. A compound according to claim 1, which is diethyl N-[4-[3-(4-amino-7H-pyrrolo[2,3-d]pyrimidin-5-yl)propyl] benzoyl]-L-glutamate.

7. A compound according to claim 1, which is N-[4-[3-(4-amino-7H-pyrrolo[2,3-d]pyrimidin-5 -yl)propyl]benzoyl]-L-glutamic acid.

8. A compound according to claim 1, which is diethyl N-[4-[3-(4-amino-2-mercapto-7H-pyrrolo[2,3-d]pyrimidin-5-yl)propyl]benzoyl]-L-glutamate.

9. A compound according to claim 1, which is N-[4-[3-(4-amino-2-mercapto-7H-pyrrolo[2,3-d] pyrimidin-5-yl)propyl]benzoyl]-L-glutamic acid.

10. A compound according to claim 1, wherein W is hydrogen or a $C_{1-6}$ alkyl group and Z is —$CH_2CH_2CH_2$—.

11. A compound according to claim 1, wherein X is an amino group and Z is —$CH_2CH_2CH_2$—.

12. A compound according to claim 1, wherein W is a mercapto group.

13. A compound according to claim 1, wherein W is a $C_{1-6}$ alkyl group.

14. A compound according to claim 1, which is a compound of the formula,

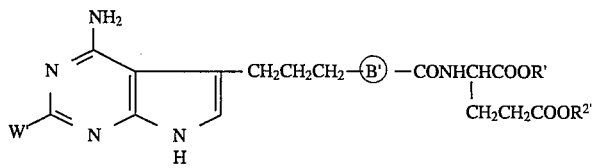

wherein W' is hydrogen, a $C_{1-4}$ alkyl or a mercapto group,

ⓑ is

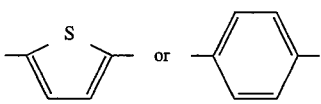

and $R^{1'}$ and $R^{2'}$ are hydrogen or a $C_{1'-6}$ alkyl group, or a salt thereof.

15. A compound according to claim 14, wherein ⓑ is

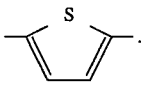

* * * * *